United States Patent [19]
Fleischhauer et al.

[11] Patent Number: 6,040,560
[45] Date of Patent: Mar. 21, 2000

[54] POWER CONTROLLER AND METHOD OF OPERATING AN ELECTRICAL SMOKING SYSTEM

[75] Inventors: Grier S. Fleischhauer, Midlothian; Charles T. Higgins; D. Bruce Losee, both of Richmond, all of Va.; J. Robert Nelson, Jr., Easton, Conn.; Robert L. Ripley, Midlothian, Va.; Masato Sano, Sumoto, Japan; David E. Sharpe, Chesterfield; Michael L. Watkins, Chester, both of Va.

[73] Assignee: Philip Morris Incorporated, New York, N.Y.

[21] Appl. No.: 08/951,255

[22] Filed: Oct. 16, 1997

Related U.S. Application Data

[63] Continuation-in-part of application No. 08/755,044, Oct. 22, 1996, abandoned.

[51] Int. Cl.[7] ............................................. H05B 1/02
[52] U.S. Cl. ........................... 219/494; 219/483; 219/501; 219/497; 219/492; 128/202.21; 131/329
[58] Field of Search ................................. 219/494, 497, 219/499, 501, 505, 483, 485, 486, 492; 131/194, 270, 271, 329, 273; 128/202.21, 202.27

[56] References Cited

U.S. PATENT DOCUMENTS

| | | | |
|---|---|---|---|
| 4,669,430 | 6/1987 | Reinold et al. | 219/509 |
| 5,004,881 | 4/1991 | Lee | 219/492 |
| 5,036,181 | 7/1991 | Fishman | 219/497 |
| 5,260,548 | 11/1993 | Todd et al. | 219/483 |
| 5,372,148 | 12/1994 | McCafferty et al. | 131/194 |

*Primary Examiner*—Mark Paschall
*Attorney, Agent, or Firm*—Charles E. B. Glenn; Kevin B. Osborne; Clinton H. Hallman, Jr.

[57] ABSTRACT

A novel controller in an electrical smoking system and method, wherein the method includes the steps of: establishing a preferred thermal pathway to be executed with each heater activation responsively to a puff on an electrically heated cigarette; configuring a power cycle in accordance with the desired thermal pathway; dividing the power cycle into at least first and second phases each having a respective, predetermined time period and total energy input for each phase; and adjusting a respective duty cycle (or other power-adjusting factor) in each phase of the power cycle responsively to a voltage reading of the power source such that the established, respective total energy input of each phase is achieved during the time period of each power cycle.

82 Claims, 17 Drawing Sheets

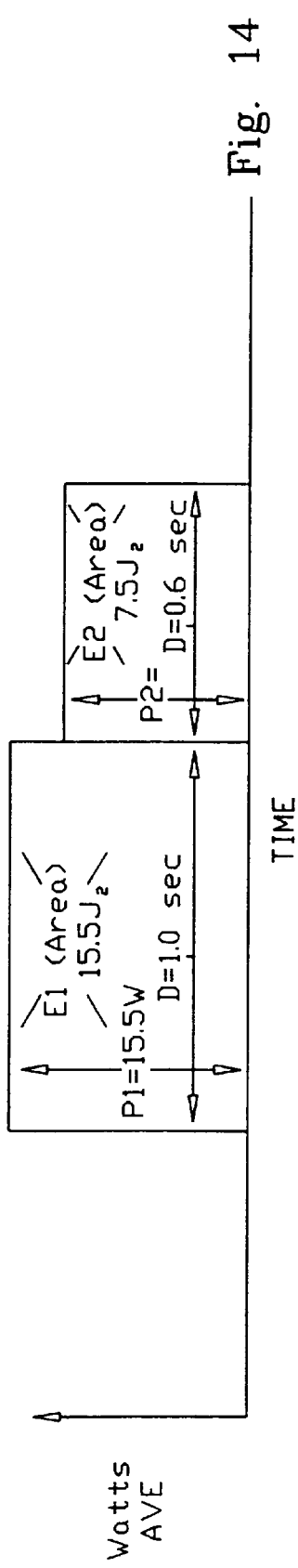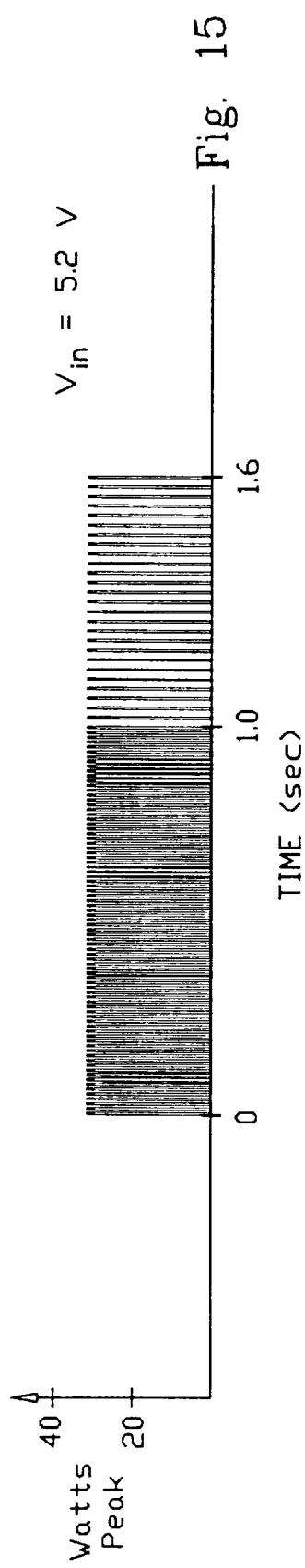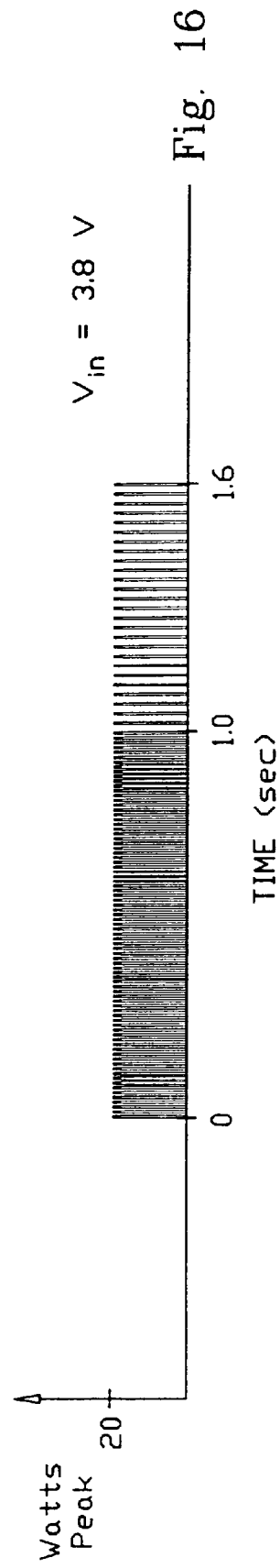

POWER CONTROLLER AND METHOD OF OPERATING AN ELECTRICAL SMOKING SYSTEM

This is a continuation-in-part of U.S. patent application Ser. No. 08/755,044 filed Oct. 22, 1996, now abandoned.

FIELD OF INVENTION

This invention relates to electrically powered smoking articles, and particularly to methods and apparatus for controlling the supply of energy to electrically powered smoking articles.

BACKGROUND OF THE INVENTION

Commonly assigned, U.S. Pat. Nos. 5,388,594, 5,505,214, and 5,591,368 disclose various electrically operated lighters and cigarettes which cooperate to significantly reduce sidestream smoke while permitting the smoker to selectively suspend and reinitiate smoking. U.S. Ser. No. 08/380,718 was preceded by a commonly assigned patent application which issued as U.S. Pat. No. 5,388,594 (PM 1697).

The preferred embodiment of the lighter in U.S. Pat. No. 5,388,594 includes a plurality of metallic serpentine heaters disposed in a configuration that slidingly receives a tobacco rod portion of the system's cigarette. The cigarette and the lighter are configured such that when the cigarette is inserted into the lighter and as individual heaters are activated for each puff, localized charring occurs at spots about the cigarette in the locality where each heater bears against the cigarette (hereinafter referred to as a "heater footprint").

In U.S. Pat. No. 5,388,594, the sequence and the amount of energy applied to each heater element during a puff cycle is regulated by a logic circuit of a controller which executes a power subroutine upon its receiving a signal from a puff sensor that a puff has been initiated. The power subroutine includes the steps of reading the voltage of the power source (batteries) at the initiation of the puff and resolving a shut-off signal to a constant Joules energy timer such that the duration of the pulse (its cycle-period) is adjusted relative to the voltage of the power source to provide the same total amount of energy (Joules) throughout the range of voltages of the battery discharge cycle. It has been discovered that this sort of power subroutine may provide the smoker a different tasting smoking experience at the extremes of the battery discharge cycle. At full battery voltage, this type of control circuit would heat a cigarette more intensively for a shorter pulse duration than a cigarette smoked near or at the conclusion of the battery discharge cycle, where the cigarette would be heated at lower power for a longer period of time (pulse cycle).

Accordingly, a need has been perceived for a controller in an electrically operated cigarette lighter which duplicates the thermal treatment of a cigarette throughout the discharge cycle of its batteries/power source.

In commonly assigned U.S. Pat. No. 5,372,148 to McCafferty et al, a controller for an electrical smoking system is disclosed having a power subroutine that includes the steps of reading battery voltage and setting an estimated pulse duration length (e.g. 1 second) and dividing the cycle into a number of intervals (e.g. 10 intervals, each 100 milliseconds), wherein the amount of energy required to generate aerosol is proportioned among the intervals in substantially equal factional amounts. During execution of the cycle, the controller monitors the amount of energy supplied to the selected heater element during each power interval and continues application of power until the correct proportional amount of energy has been delivered during the interval.

Because the power scheme of U.S. Pat. No. 5,372,148 changes cycle duration responsively to battery voltage, the power subroutine will change the thermal treatment of the cigarette as the batteries proceed through their discharge voltage cycles.

In U.S. Pat. No. 4,947,874 to Brooks et al, a smoking article includes a singular electrical resistance heating element that is impregnated with aerosol forming material and which is heated in a succession of power cycles. The article includes a current regulating circuit which provides an uninterrupted current flow immediately upon draw for about 1.5 to about 2 seconds followed by an "off" period of about 0.5 to about 1 second. The patent also proposes an alternative to an on-off time-based circuit, which alterative would include on-off and current modulating means connected to temperature sensors or other sensors that would sense either the temperature of the heating element directly or the temperature of air passing the heating element or the temperature of a second resistor having a character related to that of the aerosol carrying heating element.

The article disclosed in U.S. Pat. No. 4,947,874 is disadvantaged by its repetitively heating a singular heater and the material impregnated thereon, which creates a situation of already depleted tobacco material being heated again and again. Additionally, targeting temperature at different battery voltages may affect the rate at which energy is supplied to the heater, which in turn could affect how the article thermally treats the aerosol forming material.

OBJECTS AND SUMMARY OF INVENTION

A central object of the present invention is to provide a controller and method of applying power within an electrical cigarette system wherein the thermal pathway for enhancing smoke delivery can be established and then repeated precisely throughout the battery discharge cycle of the electrical lighter.

Another object of the present invention is to provide an electrical cigarette lighter which delivers consistent smoke throughout the discharge cycle of its batteries.

Yet another object of the present invention is to provide, in connection with the design of a lighter of an electrical smoking system, a methodology for determining a thermo-histogram that enhances smoke delivery without imposing excessive temperatures in the heater elements, together with a methodology for configuring the controller of the lighter for precise execution of the predetermined thermo-histogram so that thermal treatment of each cigarette by the lighter is precisely repeated puff after puff and cigarette after cigarette and so that the useful life of the heater elements is prolonged.

Another object of the present invention is to provide a segmented power application cycle in the lighter of an electrical smoking system, whose cycle parameters may be manipulated and matched with heater geometries so as to achieve desired subjective results in taste, impact and aroma of the smoke produced by the electrical cigarette system, so that consumer preferences may be met.

These and other objects are achieved in the present invention which provides an apparatus and method of controlling the application of power cycles in an electrical smoking system so that the smoking system provides consistent delivery from puff to puff and throughout a discharge cycle of its batteries (or other power source). Preferably, the electrical smoking system includes a lighter which comprises a source of electrical power, a plurality of heater elements and a controller for controllably communicating at least one of said heater elements with the electrical power source during a power cycle.

The novel method includes the steps of: establishing a preferred thermal pathway (or "thermo-histogram") to be executed with each heater activation responsively to a puff; and configuring the power cycle in accordance with the desired thermo-histogram. The latter step includes dividing the power cycle into at least first and second phases each having a respective, predetermined time period and total energy input for each phase. The method further comprises the steps of predetermining a discharge cycle of the power source (its upper and lower limits of operational voltage variation) and repetitively executing the configured power cycle upon demand by determining the real time voltage of the power source and adjusting a respective duty cycle (or other power-adjusting factor) in each phase of the power cycle responsively to the voltage reading such that the established, respective total energy input of each phase is achieved during the execution of each power cycle. Accordingly, the controller renders precise repetition of the desired thermo-histogram throughout the discharge cycle of the power source.

Another aspect of the present invention is an alternate method of executing a power cycle in accordance with a prescribed thermo-histogram by reading the real time loaded voltage of the power source and the real time current through the heater element and adjusting a respective duty cycle (preferably, by adjusting pulse density) in each phase of the power cycle responsively to the voltage and current readings such that the established, respective average power of each phase is achieved during the execution of each power cycle.

Yet another aspect of the present invention is the step of configuring the first and second (or more) phases of the power cycle so as to avoid excessive temperature peaks in the heater element and extend their serviceable life-expectancies.

BRIEF DESCRIPTION OF THE DRAWING

Other objects, advantages and novel features of the present invention will become apparent from the following detailed description of the preferred embodiments of the present invention when considered in conjunction with the accompanying drawing, in which:

FIG. 14 is another preferred histogram for a power cycle as established following methodology encompassed by a preferred embodiment of the present invention;

FIG. 15 is a graphical representation of peak wattage verses time as detected by a digital analyzer of the power cycle produced by the control circuit of the preferred embodiment when the battery voltage is at a fully charged state of 5.2 volts;

FIG. 16 is a graphical representation of peak wattage versus time as detected by a digital analyzer of the power cycle produced by the control circuit of the preferred embodiment when the battery voltage is at a nearly depleted state of 3.8 volts;

DETAILED DESCRIPTION OF THE PREFERRED EMBODIMENTS

Figure 1:
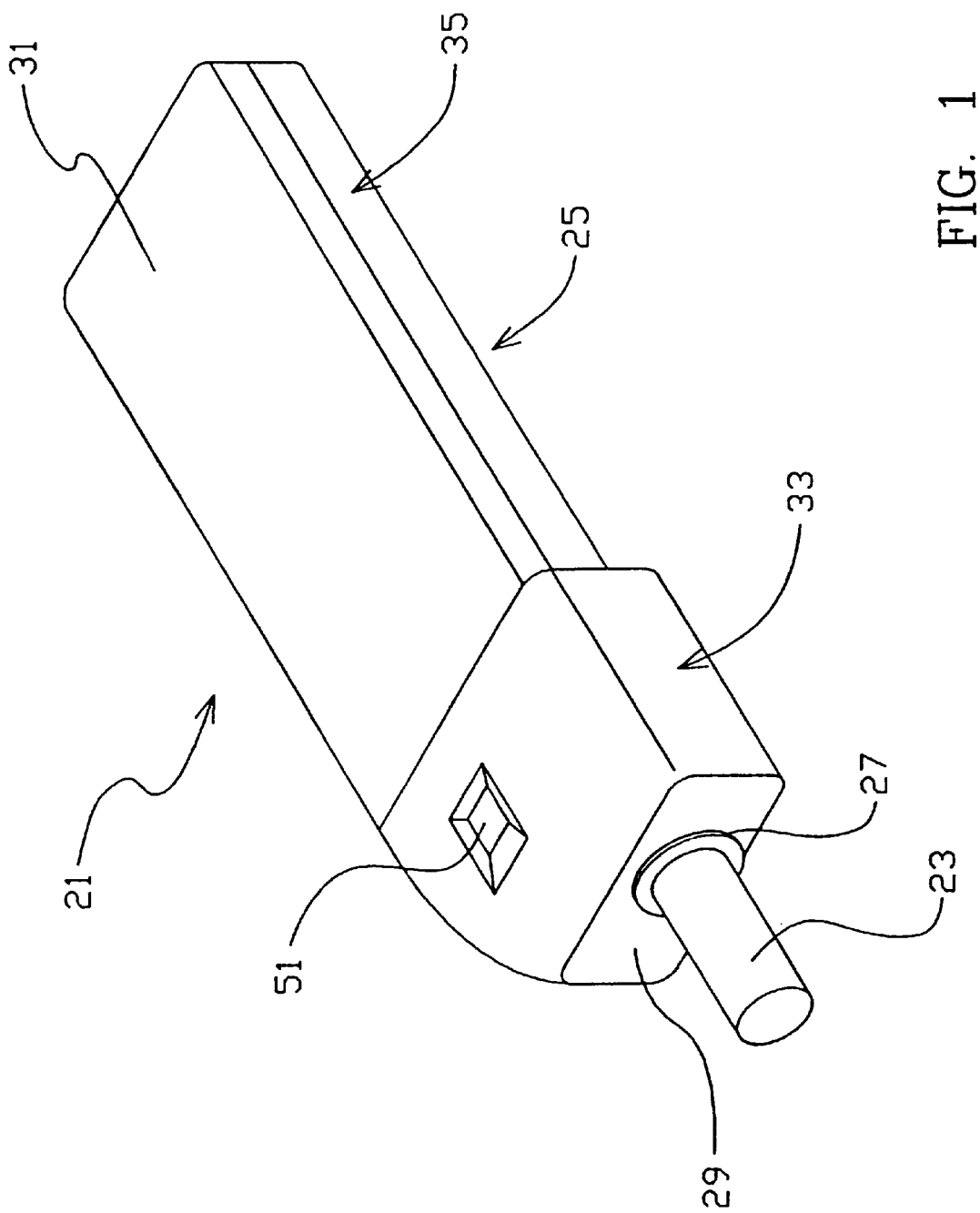
FIG. 1 is a perspective view of a smoking system in accordance with a preferred embodiment of the present invention with a cigarette thereof inserted into the electrically operated lighter.
Figure 2:
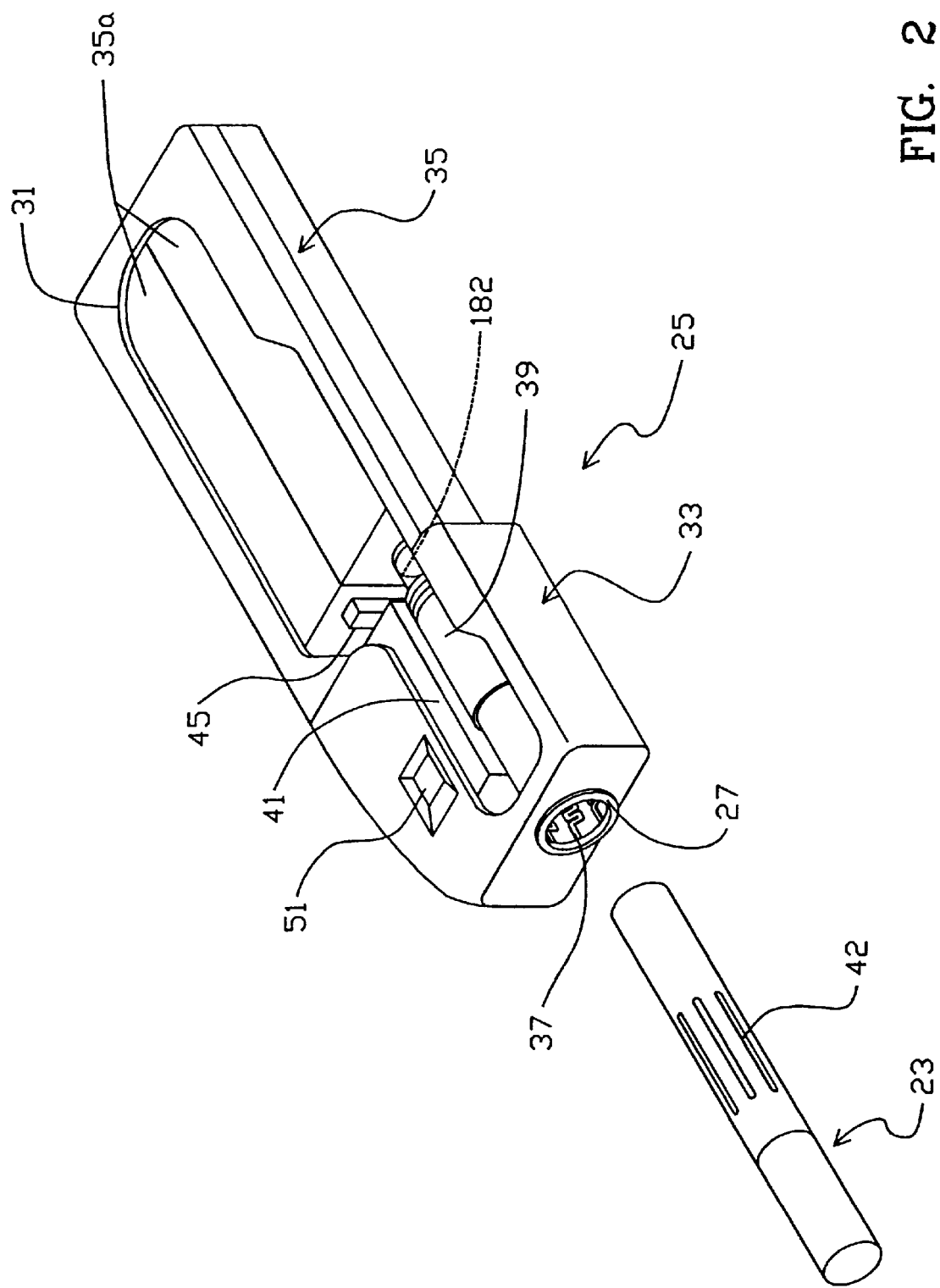
FIG. 2 is a perspective view of the smoking system of FIG. 1, but with the cigarette withdrawn from the lighter upon conclusion of a smoking.

Referring to FIGS. 1 and 2, a preferred embodiment of the present invention provides a smoking system 21 which preferably includes a partially-filled, filler cigarette 23 and a reusable lighter 25. The cigarette 23 is adapted to be inserted into and removed from a receptacle 27 at a front end portion 29 of the lighter 25. Once the cigarette 23 is inserted, the smoking system 21 is used in much the same fashion as a more traditional cigarette, but without lighting or smoldering of the cigarette 23. The cigarette 23 is discarded after one or more puff cycles. Preferably, each cigarette 23 provides a total of eight puffs (puff cycles) or more per smoke; however it is a matter of design expedient to adjust to a lesser or greater total number of available puffs.

The smoking system is described in greater detail in the commonly assigned U.S. Pat. No. 5,388,594 and in commonly assigned U.S. Pat. No. 5,388,594, which are hereby incorporated by reference in their entireties. The partially-filled, filler cigarette 23 is further described in the commonly assigned, U.S. Pat. No. 5,499,636, which is hereby incorporated by reference in its entirety.

The lighter 25 includes a housing 31 having front and rear housing portions 33 and 35. One or more batteries 35a are removably located within the rear housing portion 35 and supply energy to a plurality of electrically resistive, heating elements 37 (shown in FIG. 2) which are arranged within the front housing portion 33 adjacent the receptacle 27. A control circuit 41 in the front housing portion 33 establishes electrical communication between the batteries 35a and the heater elements 37. The preferred embodiment of the present invention includes details concerning the control circuit 41, which are discussed in greater detail beginning with reference to FIG. 7.

Still referring to FIGS. 1 and 2, preferably the rear portion 35 of the lighter housing 31 is adapted to be readily opened and closed, such as with screws or snap-fit components, so as to facilitate replacement of the batteries. If desired, an electrical socket or contacts may be provided for recharging the batteries with house current or the like. Preferably, the front housing portion 33 is removably joined to the rear housing portion 35, such as with a dovetail joint or a socket fit.

The batteries 35a are sized to provide sufficient power for the heaters 37 to function as intended and preferably comprise a replaceable and rechargeable type. Alternate sources of power are suitable, such as capacitors. In the preferred embodiment, the power source comprises four nickel-cadmium battery cells connected in series with a total, non-loaded voltage in the range of approximately 4.8 to 5.6 volts. The characteristics of the power source are, however, selected in view of the characteristics of other components in the smoking system 21, particularly the characteristics of the heating elements 37. Commonly assigned, U.S. Pat. No. 5,144,962, hereby incorporated by reference, describes several types of power sources useful in connection with the smoking system of the present invention, such as rechargeable battery sources and power arrangements which comprise a battery and a capacitor which is recharged by the battery.

Referring specifically to FIG. 2, preferably, the circuitry 41 is activated by a puff-actuated sensor 45 that is sensitive to either changes in pressure or changes in rate of air flow that occur upon initiation of a draw on the cigarette 23 by a smoker. The puff-actuated sensor 45 is preferably located within the front housing portion 33 of the lighter 25 and is communicated with a space inside the heater fixture 39 adjacent the cigarette 23 through a passageway extending through a stop 182 located at the base of the heater fixture 39. A puff-actuated sensor 45 suitable for use in the smoking system 21 is described in commonly assigned, U.S. Pat. No. 5,060,671 and commonly assigned U.S. Pat. No. 5,388,594, the disclosures of which are incorporated herein by reference. The puff sensor 45 preferably comprises a Model 163PC01D35 silicon sensor, manufactured by the MicroSwitch division of Honeywell, Inc., Freeport, Ill. Flow sensing devices, such as those using hot-wire anemometry principles, have also been successfully demonstrated to be useful for activating an appropriate one of the heater elements 37 upon detection of a change in air flow. Once activated by the sensor 45, the control circuitry 41 directs electric current to an appropriate one of the heater elements 37.

An indicator 51 is provided at a location along the exterior of the lighter 25, preferably on the front housing portion 33, to indicate the number of puffs remaining in a smoke of a cigarette 23. The indicator 51 preferably includes a seven-segment liquid crystal display. In the preferred embodiment, the indicator 51 displays the digit "8" when a cigarette detector 53 detects the presence of a cigarette in the heater fixture 39. The detector 53 preferably comprises a light sensor adjacent the open end of the cigarette receptacle 27 that detects when a beam of light is reflected off (or alternatively, transmitted through) an inserted cigarette 23. Thereupon, the cigarette detector 53 provides a signal to the circuitry 41 which, in turn, responsively provides a signal to the indicator 51. The display of the digit "8" on the indicator 51 reflects that the eight puffs provided on each cigarette 23 are available, i.e., none of the heater elements 37 have been activated to heat the cigarette 23. After the cigarette 23 is fully smoked, the indicator displays the digit "0". When the cigarette 23 is removed from the lighter 25, the cigarette detector 53 no longer detects a presence of a cigarette 23 and the indicator 51 is turned off. The cigarette detector 53 is modulated so that it does not constantly emit a beam of light, which would otherwise create an unnecessary drain on the power source 35a. A preferred cigarette detector 53 suitable for use with the smoking system 21 is a Type OPR5005 Light Sensor, manufactured by OPTEX Technology, Inc., 1215 West Crosby Road, Carrollton, Tex. 75006. In the alternative, the detector 53 may comprise a source of infrared light and a sensor opposite thereof which senses changes in infrared transmissivity across the receptacle 27.

In the alternative to displaying the remainder of the puff count, the detector display may instead be arranged to indicate whether the system is active or inactive ("on" or "off").

As one of several possible alternatives to using the above-noted cigarette detector 53, a mechanical switch (not shown) may be provided to detect the presence or absence of a cigarette 23 and a reset button (not shown) may be provided for resetting the circuitry 41 when a new cigarette is inserted into the lighter 25, e.g., to cause the indicator 51 to display the digit "8", etc. Power sources, circuitry, puff-actuated sensors, and indicators useful with the smoking system 21 of the present invention are described in commonly assigned, U.S. Pat. No. 5,060,671 (PM 1337), U.S. Pat. No. 5,388,594 and the commonly assigned, U.S. Pat. 5,505,214, all which are incorporated by reference.

Figure 8:
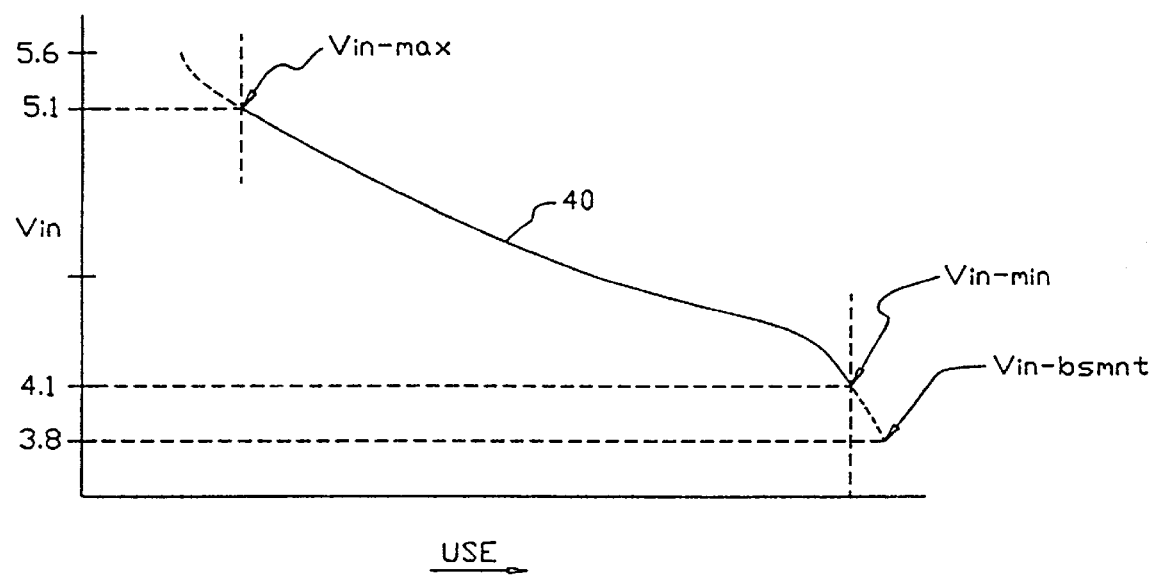
FIG. 8 is a graphical representation of a typical battery discharge cycle associated with the power source of the lighter shown in FIGS. 1 and 2.

Referring now also to FIG. 8, the preferred four cells of nickel cadmium batteries 35a typically have a voltage discharge cycle such as the one which is generally designated 40 in FIG. 8. The discharge cycle is representative of the change in output voltage ($v_{in}$) of the batteries 35a throughout their use from a fully charged state $v_{in\text{-}max}$ (preferably at or about 5.1 volts in the preferred embodiment) to a preselected minimum voltage $v_{in\text{-}min}$, preferably at or about 4.1 volts in the preferred embodiment. Preferably, the lower "cut-off" voltage $v_{in\text{-}min}$ is established slightly above a "basement" voltage $v_{in\text{-}min}$, which is known to be too low for consistent operation of the lighter 25.

Figure 3:
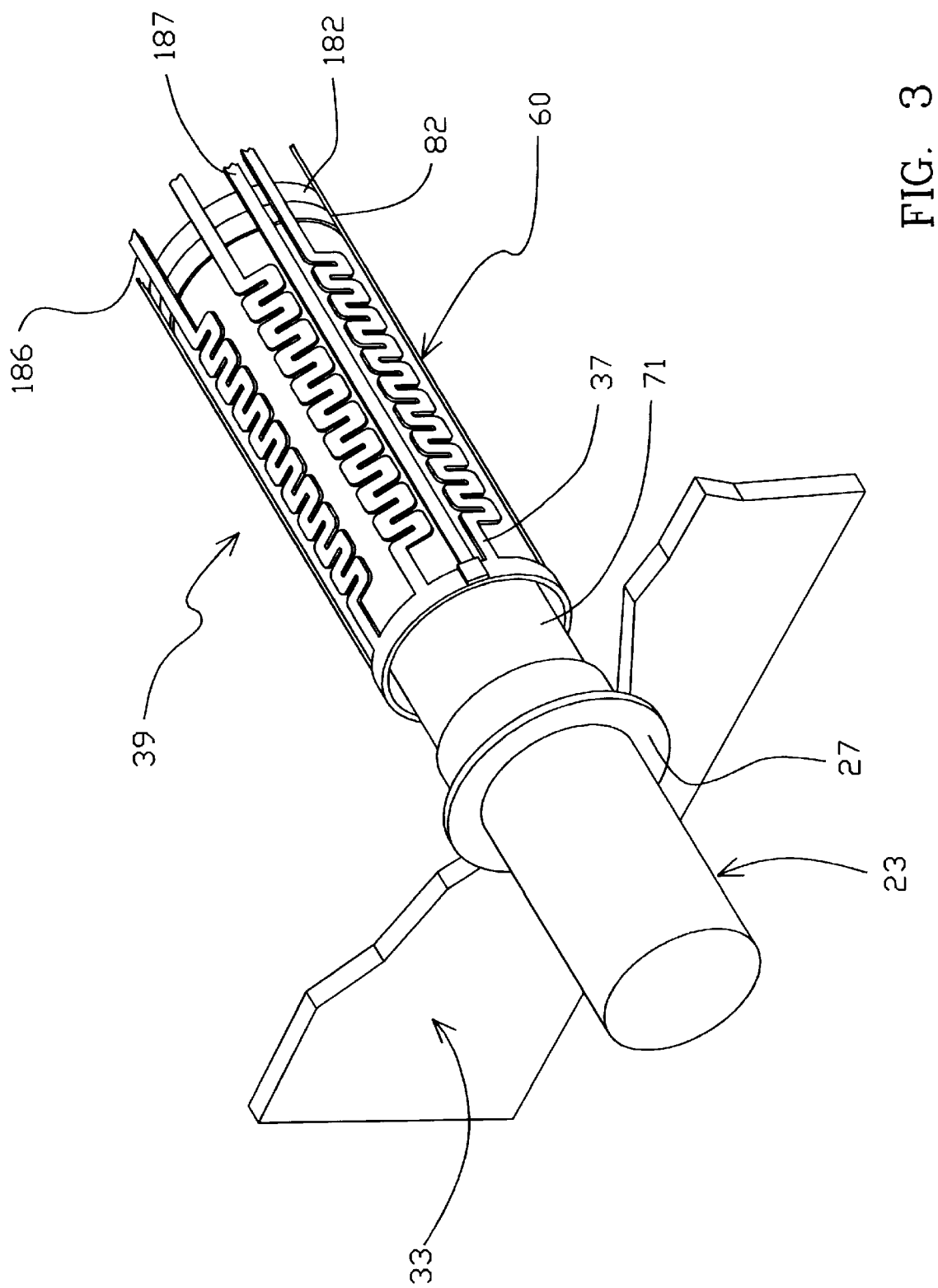
FIG. 3 is a partially broken, perspective detail of a preferred heater fixture of the lighter shown in FIG. 1 and including serpentine heater elements.

Referring now to FIG. 3, the front housing portion 33 of the lighter 25 supports a substantially cylindrical heater fixture 39 which slidingly receives the cigarette 23. The heater fixture 39 houses the heater elements 37 and is adapted to support an inserted cigarette 23 in a fixed relation to the heater elements 37 such that the heater elements 37 are positioned alongside the cigarette 23 at approximately the same location along each cigarette. The locations where each heater element 37 bears against (or is in thermal contact with) a fully inserted cigarette 23 is referred to herein as the heater footprint.

To assure consistent placement of the heating elements 37 relative to each cigarette 23 from cigarette to cigarette, the heater fixture 39 is provided with a stop 182 against which the cigarette is urged during its insertion into the lighter 25. Other expedients for registering the cigarette 23 relative to the lighter 25 could be used instead.

The front housing portion 33 of the lighter 25 also includes an electrical control circuitry 41 which delivers a predetermined amount of energy from the power source 35a to the heating elements 37. In the preferred embodiment, the heater fixture 39 includes eight circumferentially spaced-apart heating elements 37 which are concentrically aligned with the receptacle 27 so as to slidingly receive a cigarette 23. They preferably include a serpentine form. Details of the construction and establishment of electrical connections in the heater fixture 39 are illustrated and described in commonly assigned U.S. Pat. Nos. 5,388,594; 5,505,214; and 5,591,368, all which documents are incorporated herein by reference in their entireties.

Figure 4:
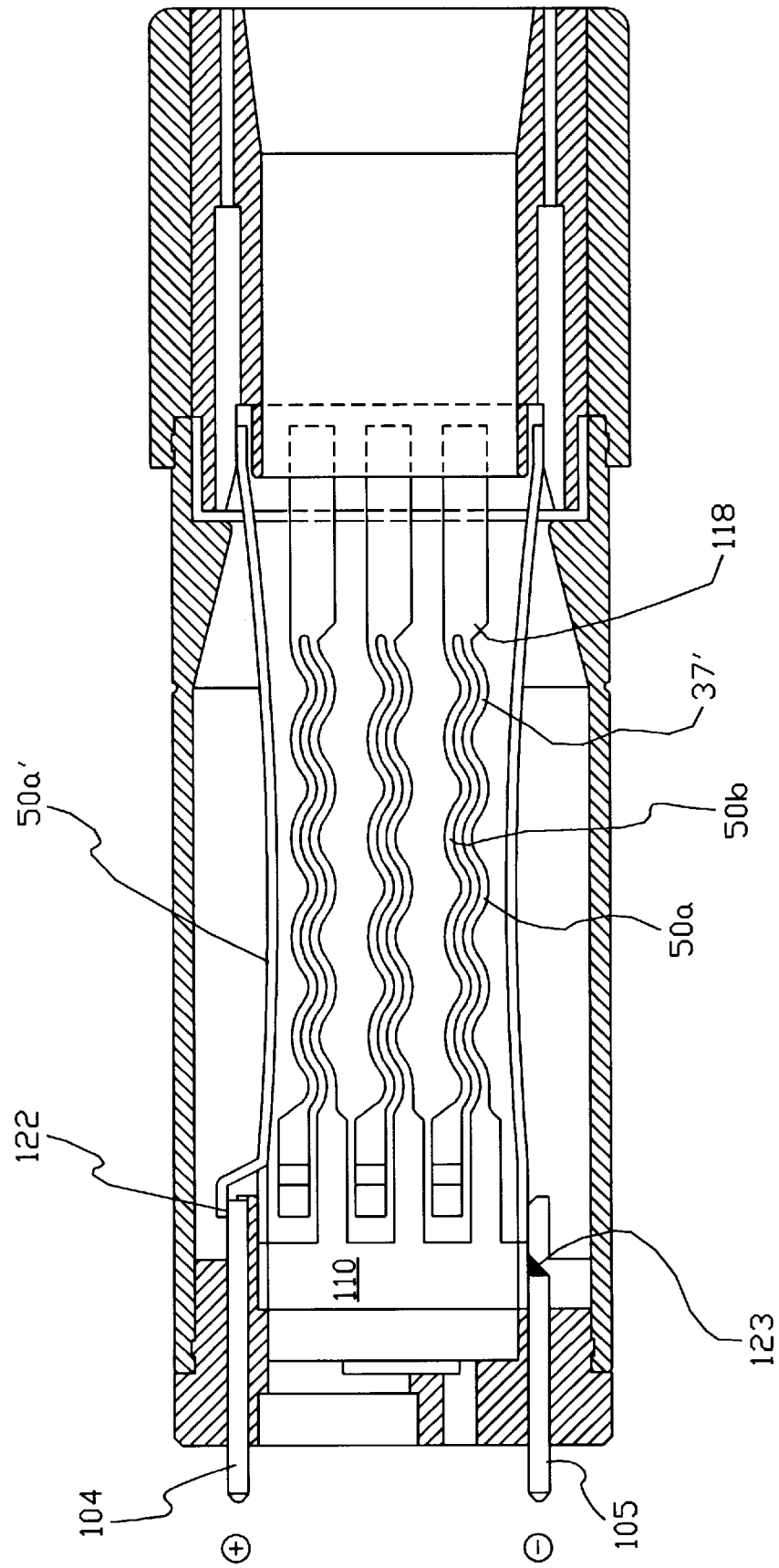
FIG. 4 is a sectional side view of an alternate, preferred heater fixture which includes wavy hairpin heater elements.

Referring now to FIG. 4, most preferably the heater elements 37 are of a design referred to herein as a wavey hairpin 37', wherein each heater element 37' includes at least first and second serpentine, elongate members 50a and 50b which are adjoined at an end portion 118. An electrical pathway through each heater fixture 37' is established, respectively, through a pin 104, a connection 122 between the pin 104 and one of the serpentine members 50a, through at least a portion of the end portion 118 to the other serpentine member 50b and back to a base portion 110 of the heater element 37'. The base portion 110 provides a common connection of all serpentine members 50b with a second pin 105 through a connection 123 between the base portion 110 and the pin 105. Further details of this heater fixture 39' are set forth in the commonly-assigned U.S. Pat. No. 5,591,368, hereby incorporated by reference in its entirety.

Figure 5:
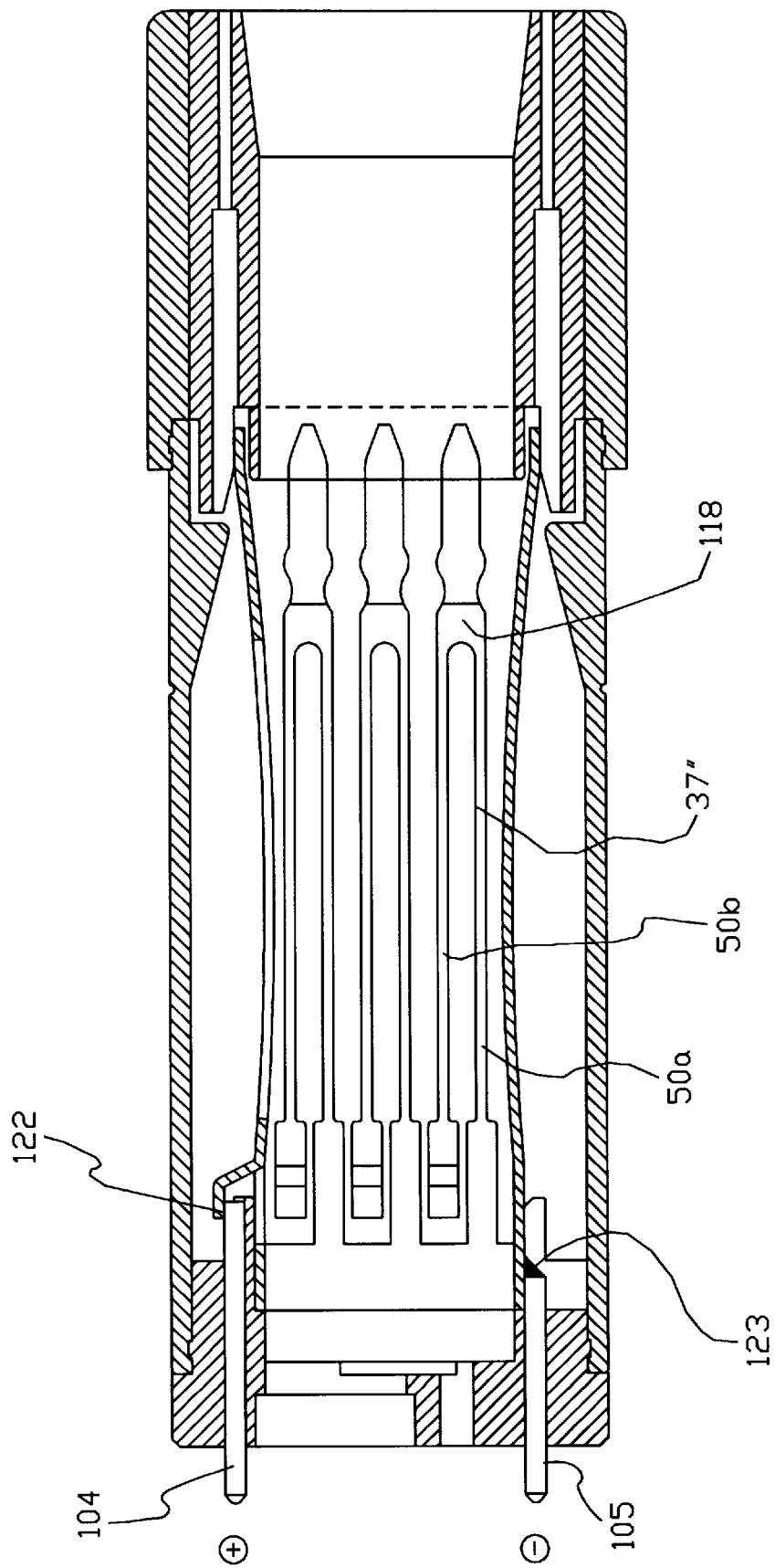
FIG. 5 is a sectional side-view of another preferred heater fixture which includes straight hairpin heater elements.

Referring now to FIG. 5, another preferred design includes heater elements in the form of a straight hairpin 37" which is connected and structured similarly to the wavey hairpin element 37' of FIG. 4, except that the elongate members 50a" and 50b" are generally straight instead of serpentine. The elongate members of both types of hairpin heaters are preferably biased inwardly to more positively engage a cigarette 23. Details of this heater fixture 39" are set forth in the same U.S. Pat. No. 5,591,368.

Referring now to FIG. 3, yet another preferred heater fixture 39 includes "singular serpentine" elements 37, each which is electrically connected at its opposite ends to a control circuit through leads 186 and 187. Details concerning this heater fixture 37 are set forth in commonly assigned U.S. Pat. No. 5,388,594 (PM 1697), incorporated by reference in its entirety.

Additional heater fixtures 37 that are operable as part of the lighter 25 include those disclosed in commonly assigned U.S. Pat. No. 5,665,262 and 5,498,855, which are incorporated herein by reference in their entireties.

Preferably, the heaters 37 are individually energized by the power source 35a under the control of the circuitry 41 to heat the cigarette 23 preferably eight times at spaced locations about the periphery of the cigarette 23. The heating renders eight puffs from the cigarette 23, as is commonly achieved with the smoking of a more traditional cigarette. It may be preferred to activate more than one heater simultaneously for one or more or all of the puffs.

Figure 6:
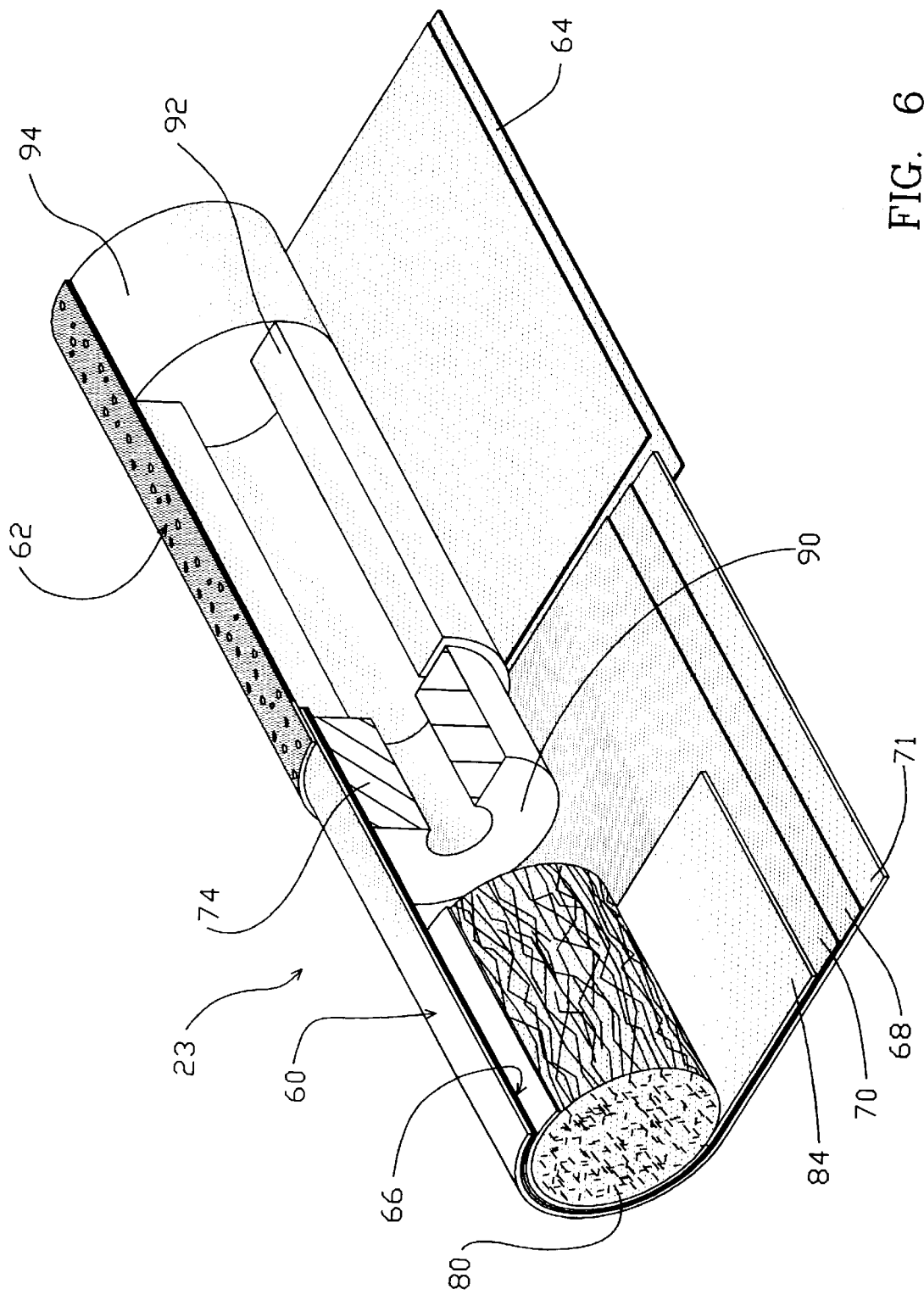
FIG. 6 is a detailed perspective view of the cigarette shown in FIGS. 1 and 2, with certain components of the cigarette being partially unraveled.

Referring now to FIG. 6, the cigarette 23 is preferably constructed in accordance with the preferred embodiment set forth in commonly assigned, U.S. Pat. No. 5,499,636, herein incorporated by reference in its entirety.

The cigarette 23 comprises a tobacco rod 60 and a filter tipping 62, which are joined together with tipping paper 64.

The tobacco rod 60 of the cigarette 23 preferably includes a tobacco web 66 which has been folded into a tubular (cylindrical) form about a free-flow filter 74 at one of its ends and a tobacco plug 80 at the other.

An overwrap 71 is intimately wrapped about the tobacco web 66 and is held together along a longitudinal seam as is common in construction of more traditional cigarettes. The overwrap 71 retains the tobacco web 66 in a wrapped condition about a free-flow filter 74 and a tobacco plug 80.

The tobacco web 66 itself preferably comprises a base web 68 and a layer of tobacco flavor material 70 located along the inside surface of the base web 68. At the tipped end 72 of the tobacco rod 60, the tobacco web 66 together with the overwrap 71 are wrapped about the tubular free-flow filter plug 74. Preferably, the tobacco plug 80 is constructed separately from the tobacco web 66 and comprises a relatively short column of cut filler tobacco that has been wrapped within and retained by a plug wrap 84.

As a general matter, the length of the tobacco plug 80 is preferably set relative to the total length of the tobacco rod 60 such that a void 90 is established along the tobacco rod 60 between the free-flow filter 74 and the tobacco plug 80. The void 90 corresponds to an unfilled portion of the tobacco rod 60 and is in immediate fluid communication with the tipping 62 through the free flow filter 74 of the tobacco rod 60.

The tipping 62 preferably comprises a free-flow filter 92 located adjacent the tobacco rod 60 and a mouthpiece filter plug 94 at the distal end of the tipping 62 from the tobacco rod 60. Preferably the free-flow filter 102 is tubular and transmits air with very little pressure drop. Other low efficiency filters of standard configuration could be used instead, however. The inside diameter for the free flow filter 92 is preferably at or between 2 to 6 millimeters and is preferably greater than that of the free flow filter 74 of the tobacco rod 60.

The mouthpiece filter plug 104 closes off the free end of the tipping 62 for purposes of appearance and, if desired, to effect some filtration, although it is preferred that the mouthpiece filter plug 104 comprise a low efficiency filter of preferably about 15 to 25 percent efficiency.

Figure 7:
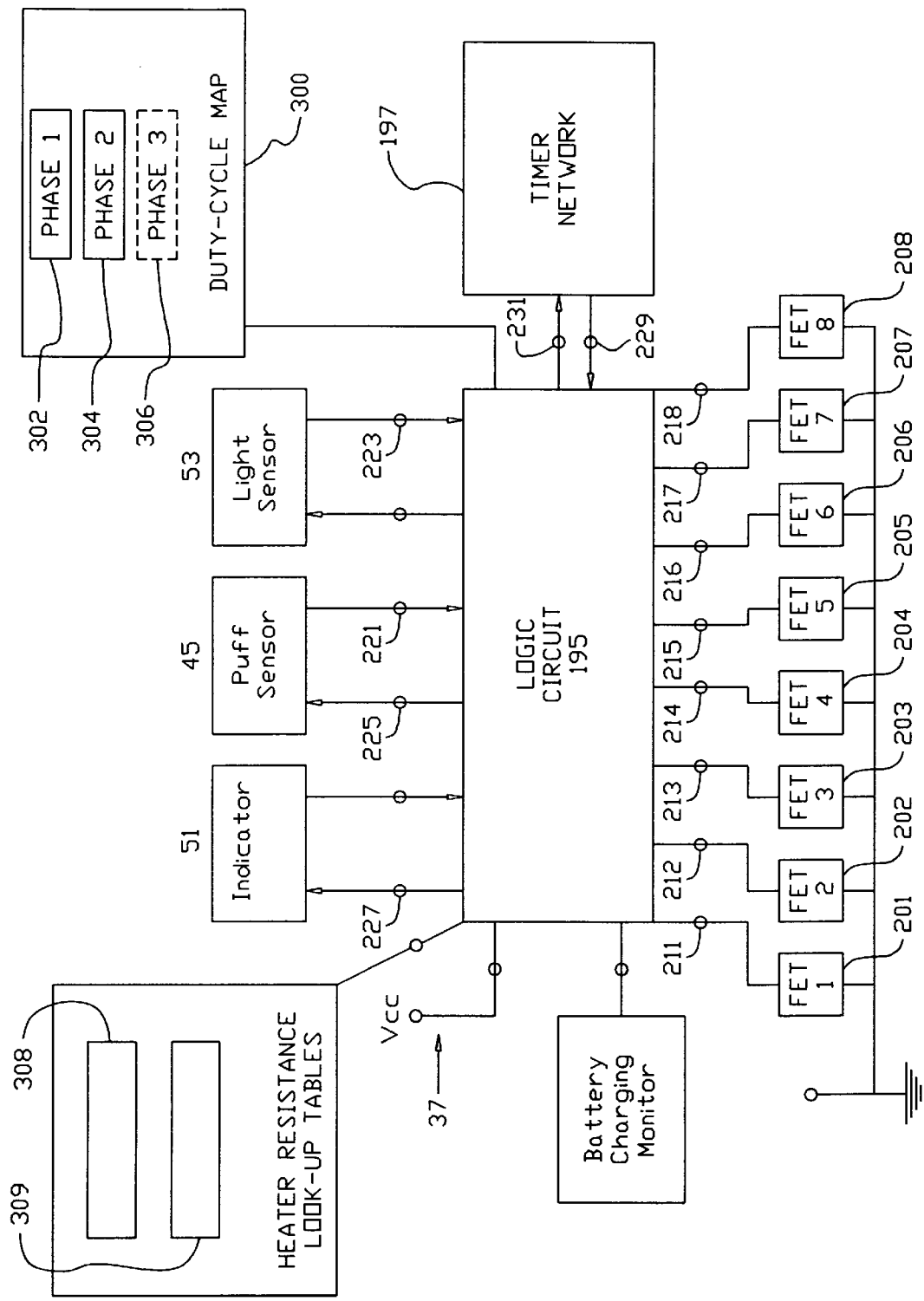
FIG. 7 is a schematic, block-diagram of a control circuit for the lighter shown in FIGS. 1 and 2.

Referring now to FIGS. 1 and 7, the electrical control circuitry 41 of the lighter 25 includes a logic circuit 195, which preferably comprises a micro-controller or an application specific, integrated circuit (or "ASIC"). The control circuitry also includes the light sensor 53 for detecting insertion of a cigarette 23 in the lighter 25, the puff sensor 45 for detecting a draw upon the inserted cigarette 23, the LCD indicator 51 for indicating the number of puffs remaining on a cigarette, the power source 37 and a timing network 197.

The logic circuit 195 may comprise any conventional circuit capable of implementing the functions discussed herein. A field-programmable gate array (e.g., a type ACTEL A1280A FPGA PQFP 160, available from Actel Corporation, Sunnyvale, Calif.) or a micro controller can be programmed to perform the digital logic functions with analog functions performed by other components. An ASIC or micro-contoller can perform both the analog and digital functions in one component. Features of control circuitry and logic circuitry similar to the control circuit 41 and logic circuit 195 of the present invention are disclosed, for example, in commonly assigned, U.S. Pat. No. 5,060,671 and U.S. Pat. No. 5,505,214, the disclosures of which are incorporated herein by reference.

In the preferred embodiment, eight individual heater elements 43 (not shown in FIG. 7) are connected to a positive terminal of the power source 37 and to ground through corresponding field effect transistor (FET) heater switches 201–208. Individual (or selected) ones of the heater switches 201–208 will turn on under control of the logic circuit 195 through terminals 211–218, respectively, during execution of a power cycle by the logic circuit 195. The logic circuit 195 provides signals for activating and deactivating particular ones of the heater switches 201–208 to activate and deactivate the corresponding ones of the heaters.

The logic circuit 195 cooperates with the timing circuit 197 to precisely execute the activation and deactivation of each heater element 37 in accordance with a predetermined total cycle period ("$t_{total}$") and to precisely divide each total cycle period into a predetermined number of phases, with each phase having its own predetermined period of time ("$t_{phase}$"). In the preferred embodiment, the total cycle period $t_{total}$ has been selected to be 1.6 seconds (so as to be less than the two-second duration normally associated with a smoker's draw upon a cigarette, plus provision for margin) and the total cycle period $t_{total}$ is divided preferably into two phases, a first phase having a predetermined time period ("$t_{phase\ 1}$") of 1.0 seconds and a second phase having a predetermined time period ("$t_{phase\ 2}$") of 0.6 seconds. The total cycle period $t_{total}$, the total number of phases and the respective phase periods are parameters, among others, that are resolved in accordance with the teachings which follow for establishing within the control circuit 41, a capacity to execute a power cycle that precisely duplicates a preferred thermal interaction ("thermo-histogram") between the respective heater element 37 and adjacent portions of the cigarette 23. Additionally, once the preferred thermo-histogram is established, certain parameters (preferably, duty cycles within each phase) are adjusted dynamically by the control circuit 41 so as to precisely duplicate the predetermined thermo-histogram with every power cycle throughout the range of voltages $v_{in}$ encompassed by the aforementioned battery discharge cycle.

The puff-actuated sensor 45 supplies a signal to the logic circuit 195 that is indicative of smoker activation (i.e., a continuous drop in pressure or air flow over a sufficiently sustained period of time). The logic circuit 195 includes a debouncing routine for distinguishing between minor air pressure variations and more sustained draws on the cigarette to avoid inadvertent activation of heater elements in response to errant signal from the puff-actuated sensor 45. The puff-actuated sensor 45 may include a piezoresistive pressure sensor or an optical flap sensor that is used to drive an operational amplifier, the output of which is in turn used to supply a logic signal to the logic circuit 195. Puff-actuated sensors suitable for use in connection with the smoking system include a Model 163PC01D35 silicon sensor, manufactured by the MicroSwitch division of Honeywell, Inc., Freeport, Ill., or a type NPH-5-02.5G NOVA sensor, available from Lucas-Nova, Freemont, Calif., or a type SLP004D sensor, available from SenSym Incorporated, Sunnyvale, Calif.

The light sensor 53 located adjacent the stop 182 supplies a signal to the logic circuit 195 that is indicative of insertion of a cigarette 23 in the lighter 25 to a proper depth (i.e., a cigarette is within several millimeters of the light sensor, as detected by a reflected light beam). A light sensor suitable for use in connection with the smoking system is a Type OPR5005 Light Sensor, manufactured by OPTEK Technology, Inc., 1215 West Crosby Road, Carrollton, Tex. 75006.

In order to conserve energy, it is preferred that the puff-actuated sensor 45 and the light sensor 53 be cycled on and off at low duty cycles (e.g., from about a 2 to 10% duty cycle). For example, it is preferred that the puff actuated sensor 45 be turned on for a 1 millisecond duration every 10 milliseconds. If, for example, the puff actuated sensor 45 detects pressure drop or air flow indicative of a draw on a cigarette during four consecutive pulses (i.e., over a 40 millisecond period), the puff actuated sensor sends a signal through a terminal 221 to the logic circuit 195. The logic circuit 195 then sends a signal through an appropriate one of the terminals 211–218 to turn an appropriate on of the FET heater switches 201–208 ON.

Similarly, the light sensor 53 is preferably turned on for a 1 millisecond duration every 10 milliseconds. If, for example, the light sensor 53 detects four consecutive reflected pulses, indicating the presence of a cigarette 23 in the lighter 25, the light sensor sends a signal through terminal 223 to the logic circuit 195. The logic circuit 195 then sends a signal through terminal 225 to the puff-actuated sensor 45 to turn on the puff-actuated sensor. The logic circuit 195 also sends a signal through terminal 227 to the indicator 51 to turn it on. The above-noted modulation techniques reduce the time average current required by the puff actuated sensor 45 and the light sensor 53, and thus extend the life of the power source 37.

The logic circuit 195 includes a PROM (programmable read-only memory) 300, which includes preferably at least two data bases or "look-up tables" 302 and 304, and optionally, a third data base (look-up table) 306. Each of the look-up tables 302, 304 (and optionally 306) converts a signal indicative of battery voltage $v_{in}$ to a signal indicative of the duty cycle ("$dc_1$" for the first phase and "$dc_2$" for the second phase) to be used in execution of the respective phase of the immediate power cycle.

Upon initiation of a power cycle, the logic circuit receives a signal indicative of battery voltage $v_{in}$, and then references the immediate reading $v_{in}$ to the first look-up table 302 to establish a duty cycle $dc_1$ for the initiation of the first phase of the power cycle. The first phase is continued until the timing network 197 provides a signal indicating that the predetermined time period of the first phase $t_{phase\ 1}$ has elapsed, whereupon the logic circuit 195 references $v_{in}$ and the second look-up table 304 and establishes a duty cycle $dc_2$ for the initiation the second phase. The second phase is continued until the timing network 197 provides a signal indicating that the predetermined time period of the second phase $t_{phase\ 2}$ has elapsed, whereupon the timing network 197 provides a shut-off signal to the logic circuit 195 at the terminal 229. Optionally, the logic circuit 195 could initiate a third phase and establish a third duty cycle $dc_3$, and the shut-off signal would not be generated until the predetermined period of the third phase ($t_{phase\ 3}$) had elapsed. The present invention could be practiced with additional phases as well.

Although the present invention can be practiced by limiting reference to the look-up tables to an initial portion of each phase to establish a duty cycle to be applied throughout the substantial entirety of each phase, a refinement and the preferred practice is to have the logic circuit 195 configured to continuously reference $v_{in}$ together with the respective look-up tables 302, 303 and 306 so as to dynamically adjust the values set for duty cycles in response to fluctuations in battery voltage as the control circuit progresses through each phase. Such device provides a more precise repetition of the desired thermo-histogram.

The timing network 197 is also adapted to prevent actuation of one heater element 43 to the next as the battery discharges. Other timing network circuit configurations may also be used, such as those described in the commonly assigned U.S. Pat. No. 5,505,214, the disclosure of which is incorporated herein by reference.

During operation, a cigarette 23 is inserted in the lighter 25 and the presence of the cigarette is detected by the light sensor 53. The light sensor 53 sends a signal to the logic circuit 195 through terminal 223. The logic circuit 195 ascertains whether the power source 37 is charged or whether the immediate voltage is below an acceptable minimum $v_{in\text{-}min}$. If, after insertion of a cigarette 23 in the lighter 25, the logic circuit 195 detects that the voltage of the power source is too low, below $v_{in\text{-}min}$, the indicator 51 blinks and further operation of the lighter will be blocked until the power source is recharged or replaced. Voltage of the power source 37 is also monitored during firing of the heater elements 37 and the firing of the heater elements is interrupted if the voltage drops below a predetermined value.

If the power source 37 is charged and voltage is sufficient, the logic circuit 195 sends a signal through terminal 225 to the puff sensor 45 to determine whether a smoker is drawing on the cigarette 23. At the same time, the logic circuit 195 sends a signal through the terminal 227 to the indicator 51 so that the LCD will display the digit "8", reflecting that eight puffs are available.

When the logic circuit 195 receives a signal through terminal 221 from the puff-actuated sensor 45 that a sustained pressure drop or air flow has been detected, the logic circuit locks out the light sensor 53 during puffing to conserve power. The logic circuit 195 sends a signal through terminal 231 to the timer network 197 to activate the timer network, which then begins to function phase by phase in the manner previously described. The logic circuit 195 also determines, by a downcount routine, which one of the eight heater elements is due to be heated and sends a signal through an appropriate terminal 211–218 to turn an appropriate one of the FET heater switches 201–208 ON. The appropriate heater stays on while the timer runs.

When the timer network 197 sends a signal through terminal 229 to the logic circuit 195 indicating that the timer has stopped running, the particular ON FET heater switch 211–218 is turned OFF, thereby removing power from the heater element. The logic circuit 195 also downcounts and sends a signal to the indicator 51 through terminal 227 so that the indicator will display that one less puff is remaining (i.e., "7", after the first puff). When the smoker next puffs on the cigarette 23, the logic circuit 195 will turn ON another predetermined one of the FET heater switches 211–218, thereby supplying power to another predetermined one of the heater elements. The process will be repeated until the indicator 51 displays "0", meaning that there are no more puffs remaining on the cigarette 23. When the cigarette 23 is removed from the lighter 25, the light sensor 53 indicates that a cigarette is not present, and the logic circuit 195 is reset.

Other features, such as those described in U.S. Pat. No. 5,505,214, which is incorporated by reference, may be incorporated in the control circuitry 41 instead of or in addition to the features described above. For example, if desired, various disabling features may be provided. One type of disabling feature includes timing circuitry (not shown) to prevent successive puffs from occurring too close together, so that the power source 37 has time to recover. Another disabling feature includes means for disabling the heater elements 43 if an unauthorized product is inserted in the heater fixture 39. For example, the cigarette 23 might be provided with an identifying characteristic that the lighter 25 must recognize before the heating elements 43 are energized.

Establishing a Preferred Thermo-Histogram

As previously discussed with reference to FIG. 7, the control circuit 41 is configured to execute a power cycle which comprises preferably first and second phases of predetermined time periods $t_1$ and $t_2$.

Fundamentally, the task undertaken here is to establish a regimen for the application of electrical power to each heater element 37 such that desired subjective attributes are achieved with the smoking of each cigarette 23, such as immediacy of delivery, impact, taste, aroma and volume.

At the start, when resolving a total time period for the power cycle, consideration is given to general observation that a smoker draws upon a cigarette for approximately a two second time period and that FTC testing procedures include a standard, two second puff.

Also, it has been discovered that if the power cycle of an electrical smoking system is continued beyond a two second time mark, a portion of the aerosol produced in the latter portion of the puff cycle may linger within the smoking system at the conclusion of smoker's draw, which situation exacerbates condensation of aerosol on the heaters.

Accordingly, operation of the electrical smoking system should preferably be curtailed at or about the terminus of a two second puff cycle so that the production of surplus aerosol is abated.

Furthermore, smoking pleasure is enhanced if the smoker is provided a subjective response most immediately upon initiation of a puff. To that end, one needs to configure an application of power such that the heater is "ramped" up to its operating temperature as quickly as possible. However, excessive peak temperatures in the heater are extremely detrimental to the life-expectancy of the heater elements 37. If the ramping step is executed too enthusiastically, the heaters may be driven to temperatures of 900° C. or more, even when the heater is loaded with a cigarette. Preferably, the heater element is heated to temperatures in the range of 680 to 780° C. and more preferably maintained in the range of 700–760° C.

Figure 9:
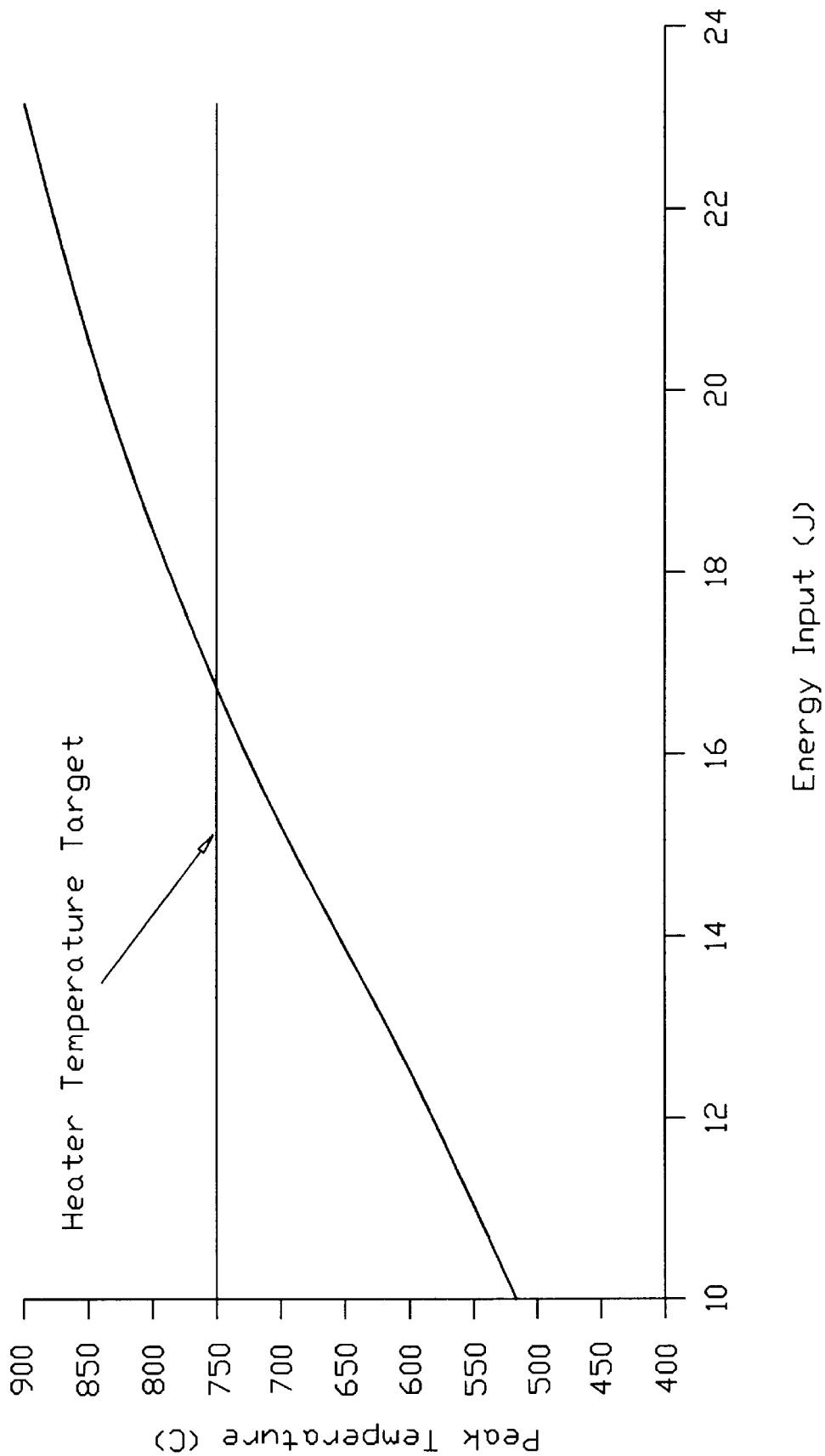
FIG. 9 is a graphical representation of the relationship between peak temperature (°C.) relative to energy input (Joules) in the heater element of the type shown in FIG. 5.

FIG. 9 shows the relationship between peak temperature in degrees Celsius relative to total energy input for a one second pulse duration with a 10 millimeter×12 millimeter straight hairpin heater element 37 (of the type shown in FIG. 5) in a loaded condition (with a cigarette). As indicated by the horizontal line representating a heater target-temperature of 750° C., a 16.5 Joule energy input during the one second pulse achieves the upper end of the desired range of heater temperatures for that particular heater type and cross-section.

Figure 10:
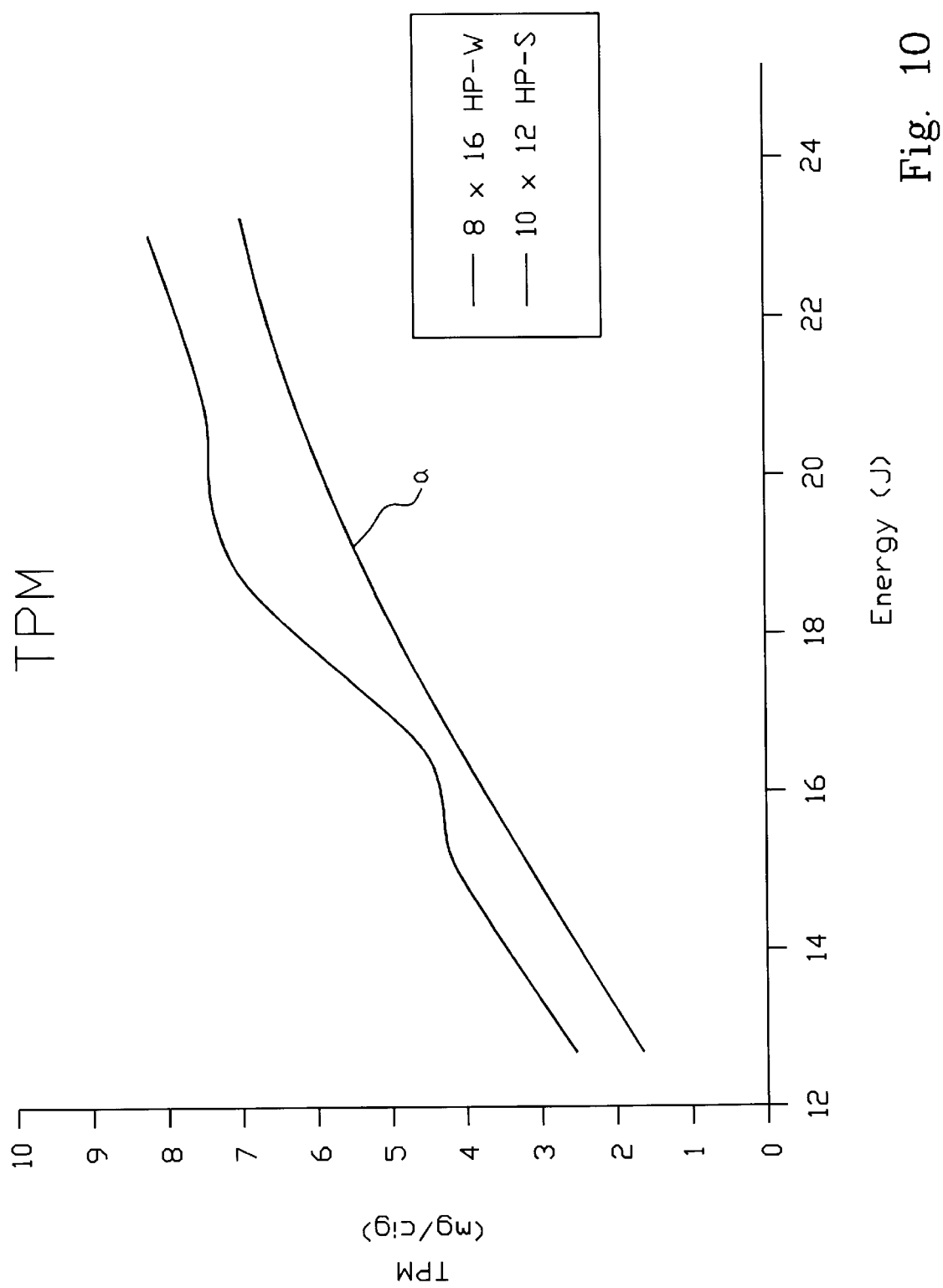
FIG. 10 is a graphical representation of the relationship between total particulate matter (TPM) in milligrams per cigarette versus the total energy input (Joules) for power cycles executed with a constant power profile and a one-second pulse, using a 10×12 millimeter straight hairpin heater element (of the type shown in FIG. 5) and an 8×16 millimeter wavey hairpin heater element (of the type shown in FIG. 4)

Referring now to FIG. 10, the line labelled "a" shows the relationship between total particulate material delivered by a cigarette 23 (in milligrams per cigarette) verses energy input to the heater in Joules in the same 10×12 millimeter (in cross-section) straight hairpin heater element 37. Line a indicates that if the energy delivery is limited to a 16.5 Joules, one-second pulse, the expected delivery in TPM will be at or about 3.75 milligrams. However, in reference back to FIG. 9, if energy input were increased to increase delivery without any other manipulation of the power cycle, then peak temperature in the heater would achieve unacceptable extremes.

Another aspect of power cycles having constant power profiles at the higher levels of total energy input is that they tended to thermally overdrive the tobacco and produce a harsh note to the smoke.

It has become apparent that a power cycle and heater had to be configured to achieve competing attributes, the capacity to achieve a rapid ramping-up in heater temperature while avoiding excessive peak temperatures in the heater, and obtaining sufficient total energy input to meet target "tar" levels without over-driving the tobacco and imparting a harsh note to the tobacco smoke. As previously discussed, the prior practice of applying a single pulse tended to create excessive peak temperatures and at the higher total energy levels to thermally overdrive (excessively pyrolyze) the tobacco.

Specifications of Preferred Thermo-Histograms

In order to meet the conflicting requirements identified above, it was resolved to divide the total power cycle into phases, with the first phase of the power cycle being dedicated to the rapid achievement of the desired operating temperature of the heater, while dedicating the second phase to completion of delivery of the desired total energy for the achievement of target tar values in a fashion avoiding peaks in heater temperature and avoiding run-away pyrolysis.

Figure 11:
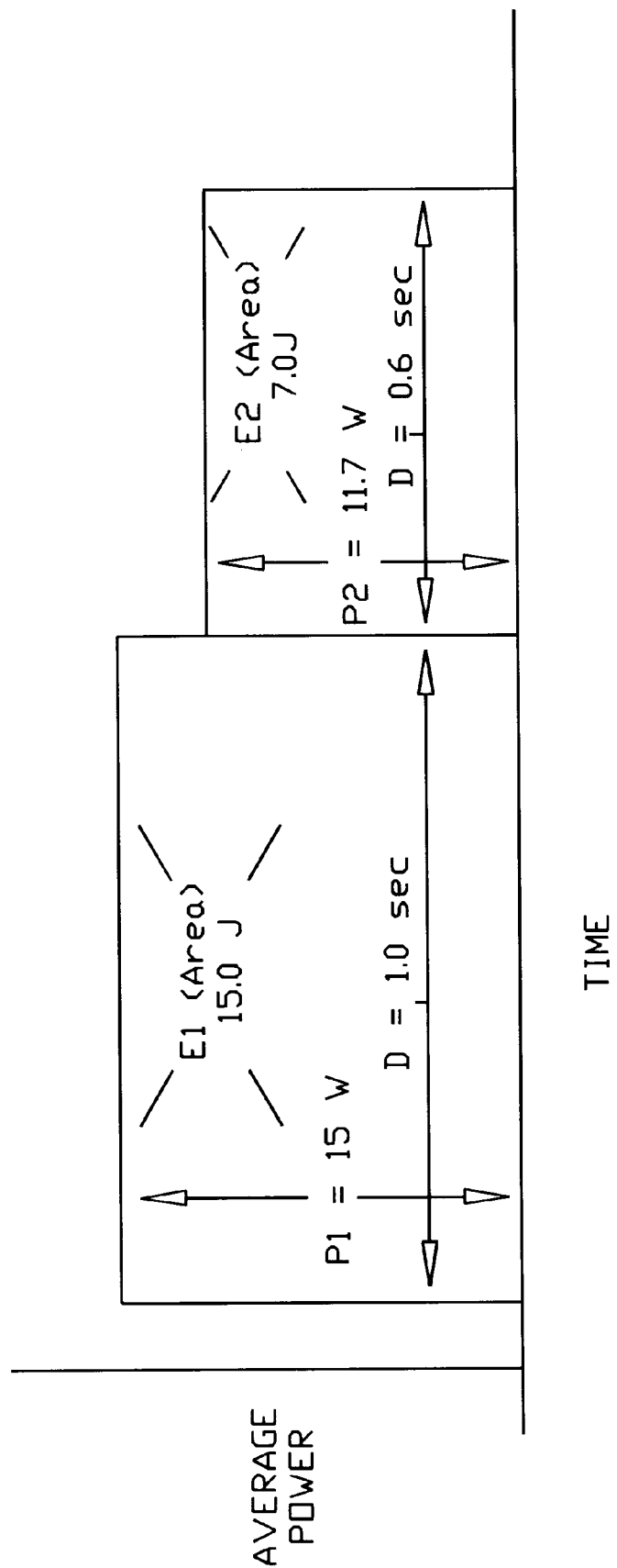
FIG. 11 is a graphical representation of a preferred two-phase thermal-histogram.

Referring now to FIG. 11, this approach has resulted in the generation of a thermo-histogram, wherein the power cycle is divided into two or more phases, each having a predetermined total energy input ($J_1$ and $J_2$) and time periods ($t_1$ and $t_2$). It has been found experimentally and analytically that good subjective results are obtained with a thermo-histogram rendering a total energy input of 22 Joules and comprising a first phase of 1 second duration ($t_1$) and a total energy of 15 Joules followed by a second phase of 0.6 seconds and a total energy input of 7 Joules.

It is to be realized that the time periods of phases and energy level may be manipulated as heater element designs are altered or their types changed. The above-described analytical and experimental approaches and further details which follow will provide guidance in resolving which combination of heater geometry and type and which thermo-histogram may provide subjectively pleasing and satisfying delivery to the smoker, while avoiding excessive thermal loading of the heaters. More particularly, the preheat cycle elevates delivery of the first puff so that the first puff is more consistent with the subsequent puffs in taste and delivery.

A simple method of resolving a thermo-histogram for operating a given heater with a given cigarette 23 for achieving a certain degree of tar delivery is to resolve the total amount of energy necessary for achieving the desired tar level (such as from resolving the relationship shown in FIG. 10) and dividing that total energy $J_t$ among two phases of a power cycle, wherein two-thirds of the total energy input is achieved in the first phase and one-third of the total energy is achieved with the second phase. This approach is rudimentary, but will usually render favorable results in many applications.

Another technique for configuring a preferred thermo-histogram is to resolve the total number of phases, the duration of each phase and the total energy $J_t$ such that the ratio of average power of the first phase (Watts$_1$) to the average power of the second phase (Watts$_2$) is in the range of approximately 2.1 to 2.7 and more preferably in the range of approximately 2.4 to 2.5.

Generally, a preferred thermo-histogram can be formulated with a first phase duration in the range of approximately 0.5 to 1.0 seconds and a first phase energy of approximately 12 to 18 Joules, together with a second phase duration in the range of approximately 1.0 to 1.5 seconds, a second phase energy of approximately 5 to 13 Joules and a grand total energy input ($J_t$) in the range of approximately 23 to 26 Joules.

More specifically, a thermo-histogram of pleasing subjective attributes includes a grand total energy input ($J_t$) of approximately 23 to 25 Joules, a first phase of approximately 0.8 second duration and a total first phase energy of approximately 14 to 16 Joules and a second phase of 1.2 seconds and a total second phase energy of 8 to 9 Joules.

A further aspect of the present invention is that once that desired thermo-histogram is established, the control circuit 41 may be configured to precisely replicate the desired thermo-histogram time and time again when one adopts the practices taught in the discussion which follows.

Figure 12:
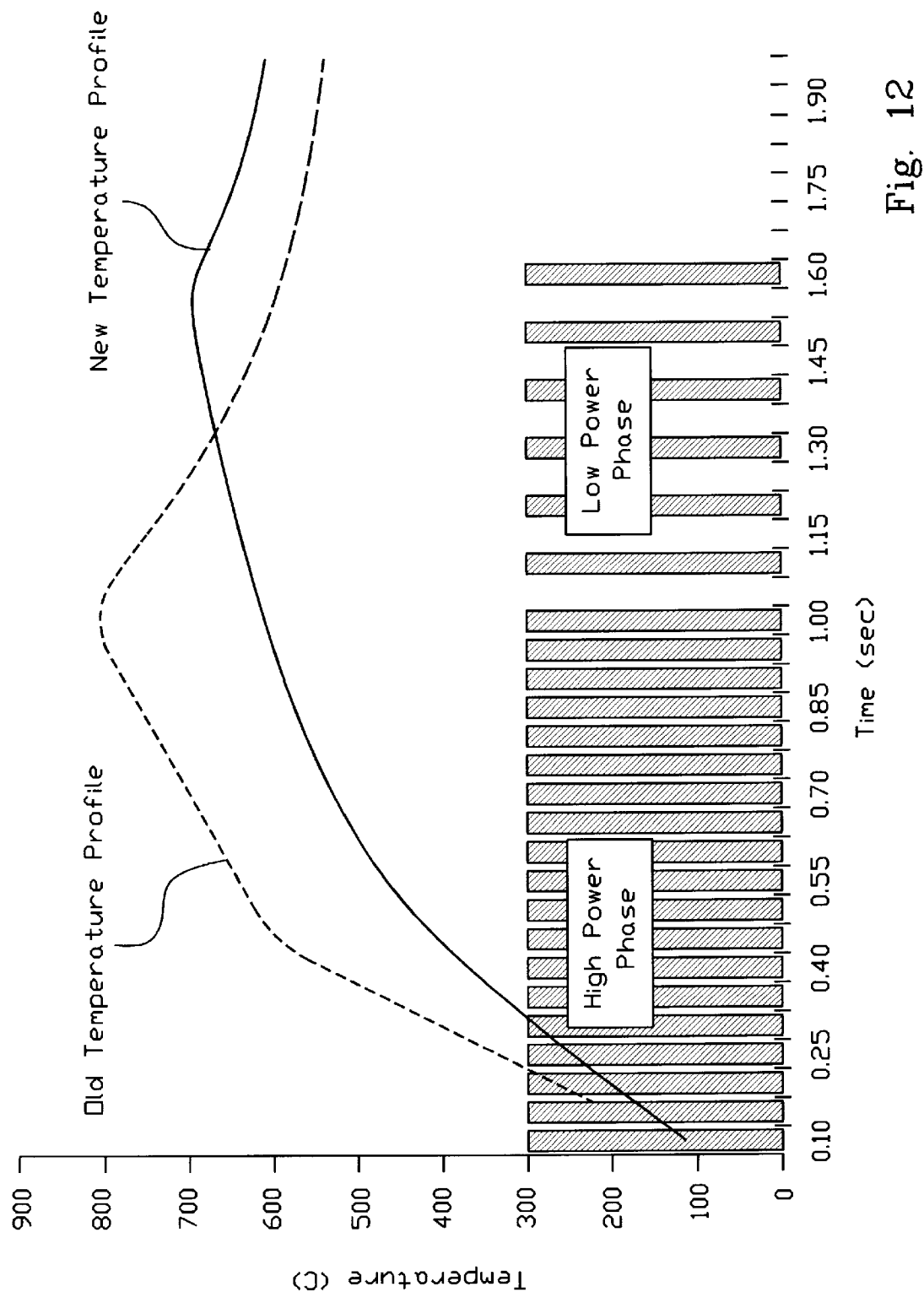
FIG. 12 is an illustration of heater temperature versus time during a first high power phase followed by a second low power phase of power modulation throughout a phased power cycle.
Figure 13:
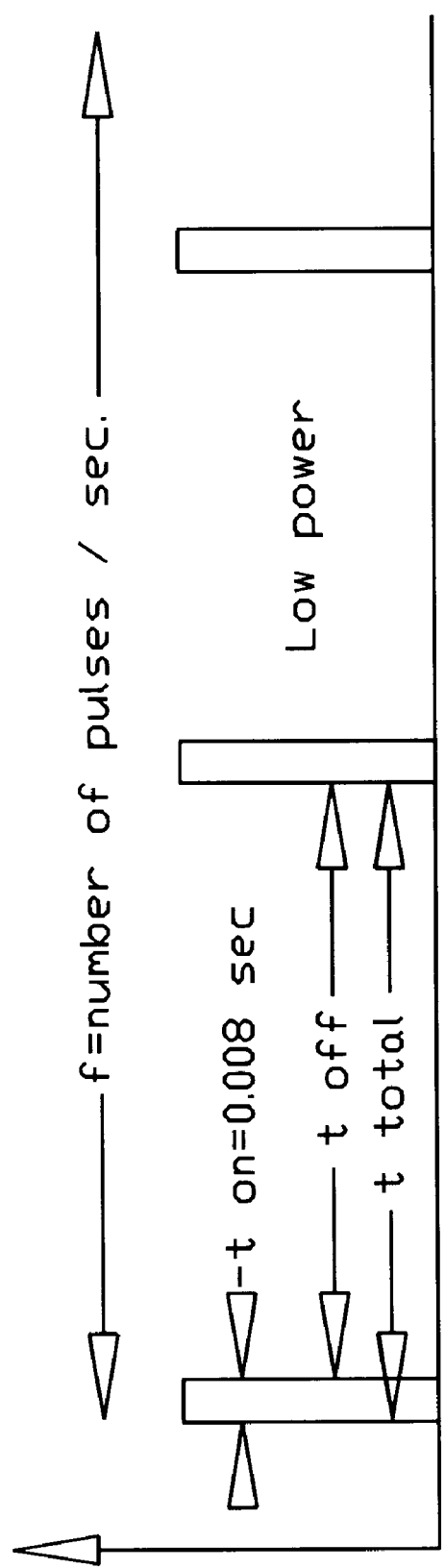
FIG. 13 is a diagram illustrating the various characteristics of a pulsed wave form produced by the logic circuit of the preferred embodiment.

Configuring the Logic Circuit for Precise Repetition of the Desired Thermo-Histogram Referring now to FIGS. 12 and 13, together with reference to FIG. 7, the logic circuit 195 of the control circuit 41 is arranged to divide each power cycle executed by the logic circuit 195 into first and second phases, each of a duration matching that established in the preferred thermo-histogram as described above. In order to arrive at the desired total energy deliveries determined for each of the thermo-histogram phases, the logic circuit 195 modulates the power application during each phase of the power cycle.

Preferably, the power modulation is in the form a pulse density modulation, wherein the logic circuit 195 repetitively generates power pulses of a predetermined incremental period of time "$t_{on}$", which pulse duration is fixed. Preferably, the pulse width "$t_{on}$" is approximately 0.008 second (8 milliseconds), but other values could be used instead. Modulating in accordance with a fixed pulse durations ($t_{on}$) is preferred because it facilitates precise execution of power cycles, particularly in that each incremental power pulse is a repetition and is not dynamically adjusted. Instead, the time between the incremental power pulses ($t_{off}$) is adjusted.

The logic circuit 195 determines the number of such pulses to be generated per second (frequency "f") in accordance with subroutine which will be detailed in the discussion which follows, so that for a given phase, the total energy delivered in that phase ($J_1$, $J_2$ or optionally $J_3$) is determined by the peak power during each of the incremental pulses times the period of each incremental pulse "$t_{on}$", times the frequency established by the logic circuit 195, times the total time allocated to that phase ($t_1$, $t_2$ or optionally $t_3$).

With these relationships, it can be established that for a given phase, for example, the first phase, frequency for the power modulation in phase one ("f1") can be resolved in accordance with the following equation:

$$f_1 = (J_1/[t_{on} \cdot t_{phase\ 1}]) \cdot (R_h/[v_{in} * (R_h/(R_h + R_c)])^2); \quad (1)$$

where $R_h$ is the resistance of the heater; $R_c$ is the resistance of the circuitry; $J_1$ is the desired total energy for phase 1 (as determined by the thermo-histogram); $t_{on}$ is the time period of each modulated pulse of power; $t_{phase\ 1}$ is the total time period of phase 1; and $v_{in}$ is the immediate voltage level of the batteries. The term $R_c$ used in the above equation is circuit resistance including leads, FET's, contacts and fuses/surge current protectors (usually between about 0.15 to 0.20 ohms). The term $R_h$ refers to heater resistance which in the preferred embodiment approaches a mean of approximately 0.65 ohms.

The term duty cycle ("dc") is the percentage of the power/energy delivered to the heater, as compared to the maximum power/energy which possibly could be delivered to the heater (a constant energy profile). Referring to FIG. 13, during the execution of a phase, for example the first phase, the logic circuit 195 resolves frequency of the first phase and then establishes that frequency by setting a counter which establishes the requisite time ("$t_{off}$") between each of the modulated pulses.

Duty cycle (dc) relates to frequency (f) as follows for each phase:

$$dc = t_{on} \cdot f / t_{phase} = t_{on}/t_{on}+t_{off}. \quad (2)$$

The above power modulation is enhanced by arranging the logic circuit 195 to dynamically monitor battery voltage ($v_{in}$) during the execution of each modulated pulse and compensating changes in the most immediately detected $v_{in}$ with changes in the counter establishing $t_{off}$. Accordingly, if the logic circuit 195 detects a drop in $v_{in}$ during execution of the first phase of a power cycle, it will reduce the period of $t_{off}$ so that the duty cycle in the first phase is increased to maintain the target total power ($J_1$) which had been established for the first phase in accordance with the desired, predetermined thermo-histogram.

Referring specifically to FIG. 7, another operational expediency in the configuration of the power cycle is to include within the logic circuit 41 a subroutine which references or "pings" the heater one or several times when a battery is recharged and/or replaced so as to obtain a voltage test-reading from the heater element 37. The resultant voltage reading is then utilized to resolve the immediate level of resistance of the heater element 37 with reference to a look-up table 308. From this determination of heater resistance ($R_{heater}$), the logic circuit 195 then references a second PROM look-up table 309 to resolve a trim energy "$\Delta J_{trim}$", which reading is used to adjust the value for the total energy predetermined for each phase ($J_{1\ adj'd} = J_1 + \Delta J_{trim}$). The control circuit then undertakes the calculation of frequency ($f_1$) for that phase using $J_{1\ adj'd}$.

Achieving Consistency in Puff Delivery Throughout the Battery Discharge Cycle

Another important aspect of the present invention is to configure the control circuit 41 such that throughout the aforementioned battery discharged cycle, the control circuit 41 consistently executes a power cycle that achieves the desired, predetermined thermo-histogram. Such feature obtains delivery of a subjectively pleasing smoke from puff to puff, but also assures that the smoking customer is delivered consistent smoking experience from cigarette to cigarette and from pack to pack, as is the expectation with the more traditional cigarettes.

This attribute is achieved through manipulation by the circuit logic 195 to adjust the duty cycles of each phase as the batteries progress through their discharged cycles so as to maintain the predetermined total energy application for each phase ($J_1$ and $J_2$) throughout the discharge cycle.

Referring back to FIG. 7, this aspect is accomplished by the logic circuit 195 when initiating the smoking of a cigarette by first reading battery voltage $v_{in}$ and referring to a duty cycle look-up map 302 for first phase of the power cycle to establish a duty cycle, $dc_1$ for that voltage $v_{in}$. This operation is an equivalent to the logic circuit 195 establishing frequency ($f_1$) in accordance with equation (1) set forth above. The logic circuit 195 progresses through phase one, and then preferably refers to a reading of $v_{in}$ before referencing the duty cycle look-up table 304 to establish a value for duty cycle $dc_2$ for the new reading of $v_{in}$. The logic circuit 195 then progresses through the execution of the second phase of the power cycle and achieves the predetermined total energy input $J_2$) as predetermined by the desired thermo-histogram. Adjustments are made dynamically for fluctuations in battery voltage during the execution of each phase as previously discussed and adjustments are made for changes in heater resistance as also described above.

The logic circuit 195 executes similar steps if an optional third phase (or fourth) is established for the desired thermo-histogram.

Preferably, a design point is established for the logic circuit 195 for establishing duty cycles at lowest most voltage $v_{in-bsmnt}$ (see FIG. 8) to be expected from the power source. Preferably, this design point is at a battery voltage ($v_{in-bsmnt}$) at some margin below $v_{in-min}$ so that the logic circuit 195 does not typically approach the lowest-most voltage nor the extreme of the look-up table 302 or 304. In the preferred embodiment, the logic circuit deactivates the lighter at a voltage of approximately 4.1 volts, even though the look-up tables extend down to 3.6 volts.

Preferred, Exemplary Embodiments

In accordance with the above teachings, it was established with a wavy hairpin heater of 8×16 cross section and a total energy input of 23 Joules, that the first phase is preferably configured to have a time period of 1.0 seconds and a total first phase energy input of 15.5 Joules. The second phase is configured to have a 0.6 second duration and include a total energy delivery of 7.5 Joules. With a four-cell battery power supply, $v_{in-max}$ was determined to be 5.1 volt, with the battery undergoing a voltage discharge cycle that achieved at its very operationally minimum voltage ($v_{in-bsmnt}$) of 3.6 volt which was used as a designed point. Operationally, and for establishing the look-up table 302 for the control circuit 41, the operational minimum voltage ($V_{in-min}$) was established at 4.3 volt, below which the logic circuit 195 would cause an indication that the battery need recharging and curtail further operation of the lighter.

As established by the above teachings, the following values were established by the control circuit 41 as set forth in table below.

TABLE I

Wavey Hairpin 8 × 16 Millimeter Cross-Section
Total Energy $J_t$ = 23

| $V_{in-max}$ = 5.1 volts | | $V_{in-min}$ = 4.3 volts | |
|---|---|---|---|
| Phase 1: | 15.5 $J_1$ energy | Phase 1: | 15.5 $J_1$ energy |
| | 52% $dc_1$ | | 83.5% $dc_1$ |
| | 1.0 second $t_{phase\ 1}$ | | 1.0 second $t_{phase\ 1}$ |
| | 15.5 watts ave. power | | 15.5 watts ave. power |
| Phase 2: | 7.5 $J_2$ | Phase 2: | 7.5 $J_2$ energy |
| | 40% $dc_2$ | | 65.5% $dc_2$ |
| | 0.6 sec $t_{phase\ 2}$ | | 0.6 sec $t_{phase\ 2}$ |
| | 12.5 watts ave. power | | 12.5 watts ave. power |

The above arrangement is derived from a design point wherein $V_{in-bsmnt}$ is established to be 3.6 volts with a 100% duty cycle in phase 1.

To further the understanding of how our modulation is arranged to replicate a desired thermo-histogram through the battery discharge cycle, FIG. 14 sets forth a desired thermo-histogram of 15.5 Joules in the first phase having a 1.0 second duration, together with a 7.5 Joules input during a second phase wherein the pulse duration is 0.6 seconds. Once the control circuit 41 has been configured in accordance with the above teachings, and in reference to FIG. 15, a digitizing signal analyzer shows the nature of the power cycle established by the control circuit 41 when executing a power cycle at 5.2 volts ($V_{in}$). Referring now to FIG. 16, when the battery voltage drops to 3.8 volts, the peak wattage falls below 20 watts and duty cycle is increased compensate so as to replicate the thermo-histogram of FIG. 14.

Figure 17:
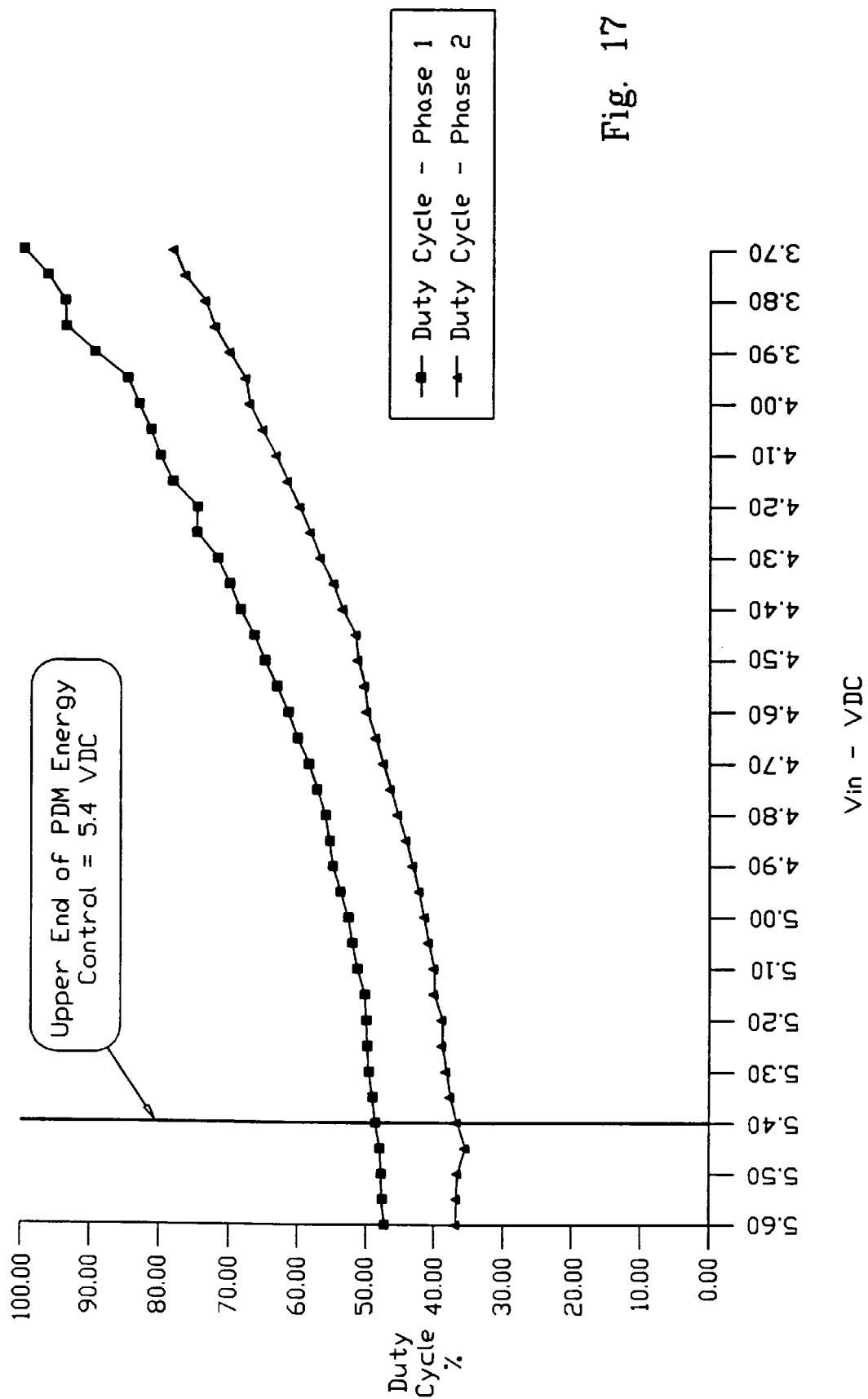
FIG. 17 is a graphical representation of duty cycles in the first and second phases of a preferred power cycle versus the battery voltage $v_{in}$.
Figure 18:
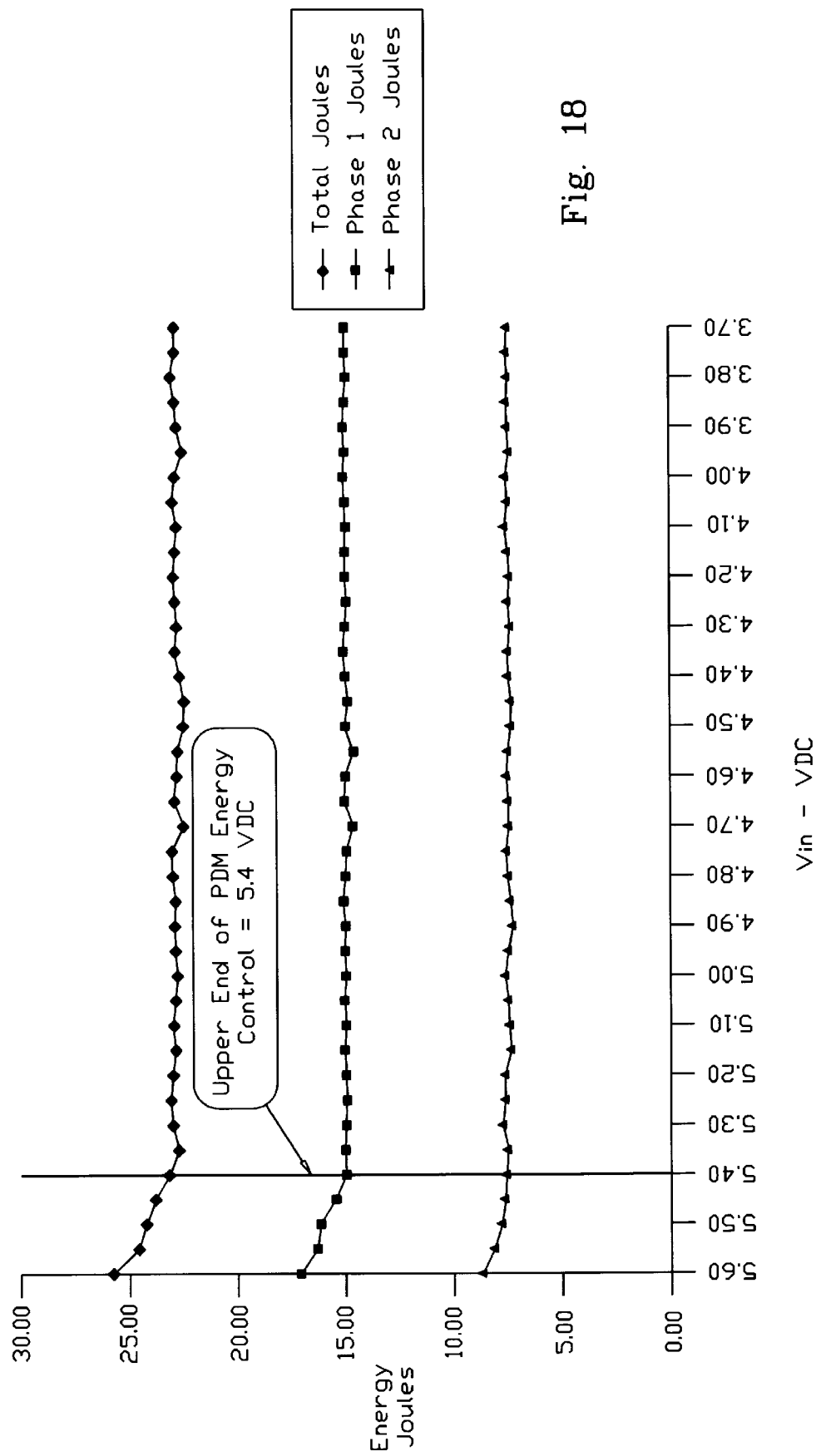
FIG. 18 is a graphical representation of energy (the total Joules and the Joules of phases 1 and 2) verses $v_{in}$.

Referring now to FIGS. 17 and 18, one can readily ascertain the precision at which the control circuit 41 of the preferred embodiment reproduces the desired step-wise application of energy from one phase to the next throughout the range of voltages associated with the battery discharge cycle.

Preferred Three-Phase Alternate Embodiments

Two phase power cycles are effective arrangements when the total Joules for the power cycle ($J_t$) are in the range of approximately 22–26 Joules. At the upper end of that range of energies, it may prove worthwhile to reconfigure the power cycle in accordance with a three-phase histogram.

For example, a smoking system 21 was arranged to mimic the flavor and delivery of a popular light cigarette having a tar delivery of 11 milligrams. The control circuit 41 of the smoking system 21 was configured to operate in accordance with the following thermo-histogram and matching power cycle:

TABLE II

| Wavey Hairpin Heater 8 × 16 mm Gap-Filler Cigarette | | |
|---|---|---|
| Phase 1 | Phase 2 | Phase 3 |
| 10.3 $J_1$ | 7.2 $J_2$ | 6.8 $J_3$ |
| 0.5 sec $t_{phase\ 1}$ | 0.5 sec $t_{phase\ 2}$ | 0.6 sec $t_{phase\ 3}$ |
| 20.6 watts$_{ave}$ | 14.4 watt$_{save}$ | 11.3 watts$_{ave}$ |

An equivalent two-phase power cycle and thermo-histogram was established as follows:

A first phase of 10.3 Joules at 20.6 watts in a 0.5 second $t_{phase1}$, together with a 13.6 Joules 1.0 second phase. The latter is an instance where both the time period of each phase and the total Joules delivered were manipulated until a histogram was achieved that rendered a desired level of delivery together with the desired subjective attributes (taste and impact).

True-Power Control

In the prior embodiments, the power cycle is divided into at least first and second phases each having a respective, predetermined time period and total energy input for each phase. They accommodated the discharge cycle of the power source (its upper and lower limits of operational voltage variation) by repetitively executing the configured power cycle upon demand by determining the real time loaded voltage of the power source and adjusting a respective duty cycle (or other power-adjusting factor) in each phase of the power cycle responsively to the voltage reading such that the established, respective total energy input of each phase is achieved. Battery voltage $v_{in}$ was read and the respective duty cycle was determined upon reference to a look-up table (ROM).

The prior embodiments are particularly suited where the various heater elements 37 can be manufactured such that their electrical resistivities fall within acceptably close tolerances. However, with certain heater materials and/or manufacturing techniques, the resistances may vary from heater to heater. The following true-power control cycle was established to provide precise execution of power cycles regardless of differences in resistances amongst the heater elements 37. The arrangement also includes a first and second power phase array, wherein the first phase is divided into three sub-phases. Each has its own defined phase duration $t_{1a}$, $t_{1b}$, $t_{1c}$, and $t_2$; each has its own predetermined ("target") average power level $p_{1a}$, $p_{1b}$, $p_{1c}$, and $p_2$; and consequently, each has its own resultant, total energy $J_{1a}$, $J_{1b}$, $J_{1c}$, and $J_2$.

Figure 19:
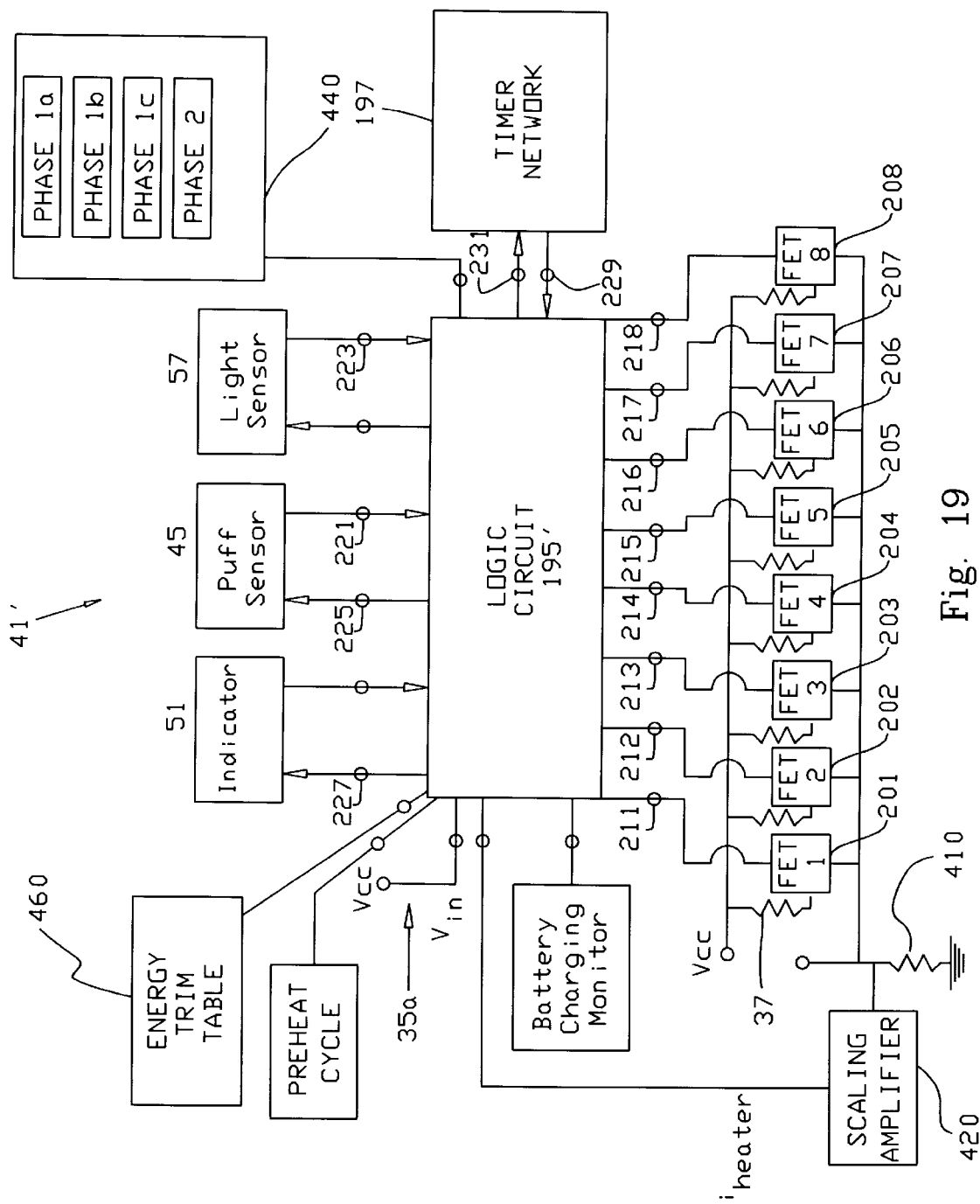
FIG. 19 is a schematic, block-diagram of a control circuit for the lighter shown in FIGS. 1 and 2, with the control circuit arranged in accordance with another preferred embodiment of the present invention.

Referring to FIGS. 13 and 19, the power modulation is in the form of a pulse density modulation, wherein the logic circuit 195' repetitively generates power pulses of a predetermined incremental period of time "$t_{on}$", which pulse duration is fixed. Preferably, the pulse width "$t_{on}$" is approximately 0.008 second (8 milliseconds), but other values could be used instead. The logic circuit 195' determines the off-times between pulses in accordance with a subroutine which will be detailed in the discussion which follows, so that for a given phase, the execution of power pulses with off-times established by the logic circuit 195' provides the target average power for that phase (e.g., $p_{1a}$).

Referring particularly to FIG. 19, a shunt resistor 410 and a scaling amplifier 420 are provided in the control circuit 41' so as to provide the logic circuit 195' a signal indicative of the current ("$i_{heater}$") that is passing through any of the heater elements 37 undergoing a power cycle. As in the previous embodiments, the logic circuit 195' is arranged to receive a signal indicative of the voltage level $v_{in}$ of the power source 35a, which is indicative of the voltage across the heater element 37 undergoing the power cycle.

In the control circuit 41', the logic circuit 195' is arranged to address a look-up table 440 which sets forth, for each phase (1a, 1b, 1c and 2), digital equivalents of the target average power levels $p_{1a}$, $p_{1b}$, $p_{1c}$, and $p_2$ and $p_2$ and the predetermined phase durations $t_{1a}$, $t_{1b}$, $t_{1c}$, and $t_2$.

Upon initiation of a power cycle, the logic circuit 195' references the look-up table 440 to register the respective target average power level for the phase (e.g., $p_{1a}$) and its phase duration (e.g., $t_{1a}$); sets a digital timer or equivalent in accordance with the value provided for phase duration (e.g., $t_{1a}$); initiates the first power pulse (of 8 milliseconds) to the selected heater element 37; and obtains immediate signals indicative of battery voltage ($v_{in}$) and heater current ($i_{heater}$). Because the mathematical product of the signal values for battery voltage $v_{in}$ and heater current $i_{heater}$ is proportional to the instantaneous power at the selected heater element 37, the logic circuit 41' can rapidly resolve a $t_{off}$ (or duty cycle $dc_{1a}$) at which the target average power of the particular phase (e.g., $p_{1a}$) is achieved at that instantaneous heater current ($i_{heater}$) and battery voltage ($v_{in}$) within the time provided by the phase duration (e.g., $t_{1a}$). The logic circuit 195' is programmed to execute this step in accordance with the following fundamental relationship:

$$t_{off} = (i_{heater} \cdot v_{in} \cdot t_{on} / p_{phase}) - t_{on}$$

wherein $p_{phase}$ is the respective target power level ($p_{1a}$, $p_{1b}$, $p_{1c}$, or $p_2$).

Accordingly, $t_{off}$ is first resolved during execution of the first incremental power pulse of the phase (e.g., phase 1a). Preferably, it is resolved again and again during each of the subsequent power pulses of the phase in the same manner so that the duty cycle is dynamically adjustable throughout the phase in execution.

Upon lapse of the timed phase duration (e.g., $t_{1a}$), the logic circuit 41' enters the next phase (e.g., phase 1b); looks-up the respective target average power for the new phase (e.g., $p_{1b}$) and its phase duration ($t_{1b}$); initiates a first power pulse (of 8 milliseconds) to the same selected heater element 37; and resolves the $t_{off}$ (or duty cycle $dc_{1b}$) in the same manner as previously described. The process is repeated for each of the subsequent phases until the power cycle is completed.

This form of power management provides precise duplication of the desired power profile and automatically compensates for differences in the electrical resistances amongst the heater elements 37 and for intermittent fluctuations of battery voltage during execution of a power cycle. It also maintains accurate power/energy delivery irrespective of load temperature or dynamic shifts in the resistance of the heater elements 37.

Preferably, when the duty cycle (e.g., $dc_{1a}$) in any phase or subphase (except the last) reaches 100% due to declining loaded battery voltage ($v_{in}$), the next phase (e.g., phase 1b) is commenced at an elevated duty cycle, preferably at a 100% duty cycle, and proceeds at the elevated duty cycle (100%) throughout a time increment Tx such that the total delivered energy delivered during Tx not only compensates for the energy missed in the preceding phase but also applies the energy increment as originally scheduled for the Tx portion of the subsequent phase. At the conclusion of Tx, the duty cycle is adjusted as previously described so that the average power (e.g., $p_{1b}$) is delivered by the end of the phase, if possible, or in the remaining phases.

If the loaded voltage is such that 100% duty cycle is required for all the phases, operation may continue (with decreased total energy) as long as the battery loaded voltage ($v_{in}$) remains at or above the low cutoff voltage. Execution of puff cycles is curtailed if the loaded voltage ($v_{in}$) falls below the low cut-off voltage.

It is to be understood that the value of total energy in a given phase (e.g., $J_{1a}$ of phase 1) and the target average power of the phase (e.g., $p_{1a}$) are indicative/proportional to each other, because the latter equals the former divided by time, and time is a fixed quantity for each phase (e.g., $t_{1a}$). Accordingly, the digital executions of the logic circuit 195' for the dynamic resolution of $t_{off}$ (or duty cycle) can be undertaken as described above using given values of target power and phase duration or alternatively, with given values of total energy per phase, together with the set of given phase durations.

A Preferred Power Profile

As in the prior, preferred embodiments, the present preferred power profile is divided in first and second phases wherein a greater portion of the grand total of energy is applied in the first phase and wherein the second phase is longer than the first. However, in the power profile set forth below, the first phase is divided into three sub-phases 1a, 1b and 1c of progressively decreasing target levels of total energy and power. This power scheme of sub-phases 1a, 1b and 1c applies the greatest amount of energy in the first sub-phase (1a) so as to quickly initiate a climb in heater temperature. The subsequent sub-phases (1b, 1c) provide lesser and lesser quantities of energies so that the system does not thermally overdrive the heater elements and cause excessive peak temperatures. Whereas the sub-phases 1a, 1b and 1c of the power cycle are arranged to promote a quick climb in heater temperature, the second phase is configured more toward sustaining an elevated heater temperature than to rapidly elevating heater temperature. Accordingly, it has a longer duration than any of the first sub-phases, and it applies a much lower average power level than any of the sub-phases 1a, 1b and 1c taken individually.

TABLE III

| Phase | Phase Time (Sec.) | Phase Energy (Joules) | Power During The Phase (Watts) |
|---|---|---|---|
| 1a | 0.25 | ~5.1 | ~20.5 |
| 1b | 0.25 | ~4.9 | ~19.4 |
| 1c | 0.25 | ~4.8 | ~19.1 |
| 2 | 1.2 | ~8.4 | ~7.0 |
| Totals | 1.95 | ~23.2 | N/A |

Although the above power schedule is preferred, one of ordinary skill in the pertinent art would readily realize upon a reading of this disclosure that other power profiles might be constructed having entirely different values than those specifically provided above, yet by their proportions of values provide functionally comparable effects, including provision for rapid heating of a heater element without incurring excessive peak temperatures and applying heat to a cigarette such that the cigarette is thermally driven in accordance with a preferred thermo-histogram as has been taught herein.

Referring back to FIG. 19, optionally the logic circuit 195' includes a second look-up table 460 ("energy trim table") comprising a listing of offsets ("$\Delta J_{e-trim}$") for each of the heater elements 37. The offsets comprise slight adjustments to target total energies ($J_{1a}$, $J_{1b}$, $J_{1c}$, or $J_2$) for each heater element 37 such that as a heater element undergoes execution of a power cycle, the target total energies from the above table ($J_{1a}$, $J_{1b}$, $J_{1c}$, and $J_2$) are each adjusted upwardly or downwardly by $\Delta J_{e-trim}$ depending upon whether the connections ("traces") to control logic circuitry 41' of the heater element is longer (with greater circuit losses) or shorter (with lesser circuit losses) than the mean. For those heater elements of greater circuit losses, the target energy levels (or target average powers) are adjusted upwardly so as to overcome the extra losses. The opposite is done for those heater elements of lesser circuit losses. Accordingly, the application of the offsets $\Delta J_{e-trim}$ enhances uniformity in the performance of the heater fixture from heater element to heater element. It also enhances precision in the execution of the power cycles in accordance with the prescribed power profile. In the preferred embodiment the values for $\Delta J_{e-trim}$ amongst the heater elements are in the range of –0.05 Joule to 0.08 Joule, but different circuit applications might require a different range of values.

Preheat Power Cycle

As previously explained, the logic circuit 195' cooperates with the cigarette detector 57 to detect the instant when a cigarette 23 is inserted into the heater fixture 39 of the lighter 25. Thereupon, the logic circuit 195' is readied for executing puff actuated power cycles as described above in cooperation with the puff sensor 45.

Referring again to FIG. 19, it is preferred that a logic circuit 195' be provided with a preheat cycle routine 480 which is operative between the instant that the light sensor 57 detects insertion of a cigarette and when the puff sensor 45 is enabled for executing puff-actuated power cycles.

Preferably, the preheating subroutine includes a portion of the logic circuit 195' being configured to execute a ⅛ second firing of each heater element 37 in succession, preferably one immediately after another. For the preferred embodiment having eight heater elements 37, the preheating cycle is executed within a grand total time of approximately one (1) second. Preferably, the logic circuit is configured to complete an execution of the preheating cycle prior to initiating any puff-actuated power cycle. The relatively short duration of the preheating cycle (one second) avoids delay in the lighter being ready and enabled to execute puff actuated power cycles. However, longer or shorter total times for the preheat cycle ($t_{preheat}$) may be implemented if desired, and the power pulse to each heater need not be an identical fraction of the total preheat cycle time $t_{preheat}$.

Preferably, the entire preheat cycle provides a target total energy level $J_{preheat}$) in the range of approximately 5 to 25 Joules, more preferably in the range of approximately 10 to 25 Joules and most preferably approximately 17 Joules per preheating cycle.

The preheat cycle routine 480 is preferably executed at approximately 1 second after confirmation that a cigarette has been inserted into the lighter 25 by the cigarette detector 57.

It has been found that he preheat cycle thermally pretreats the tobacco rod of the cigarette 23 such that a fuller, more subjectively pleasing response is obtained from the cigarette 23 upon execution of the puff-actuated power cycles.

Optionally, execution of each power pulse may be controlled utilizing power modulation techniques as described above, wherein the total Joules ($J_{preheat}$) is fixed, the duration of the preheat pulse cycle is fixed ($t_{preheat}$) and where the battery voltage ($v_{in}$), or alternatively, both battery voltage ($v_{in}$) and heater current ($i_{heater}$) are read and duty cycle is adjusted by the logic circuit 195' responsively to the readings so that the desired preheat energy ($J_{preheat}$) is obtained.

While this invention has been illustrated and described in accordance with preferred embodiments, it is recognized that variations and changes may be made therein without departing from the invention as encompassed in the claims. In that regard, the type of heater elements 37 may instead comprise lasers or inductive elements or any other device to transfer heat to a cigarette during a puff cycle. Furthermore, although the preferred embodiments teach manipulation of the total energy and time period for two or more phases to achieve desired deliveries and taste in a cigarette 23, other parameters might be varied. In like fashion, parameters other than duty cycles of the several phases of the power cycle may be adjusted to effect precise duplication of a desired thermo-histogram during execution of each power cycle throughout a voltage discharge cycle of batteries. Additionally, the device might use power sources other then batteries. Furthermore, dynamic adjustments of each phase in response to changes in duty cycle and/or resistance in the heaters might be accomplished with arrangements other than PROM look-up tables. For instance, parameters may be varied in accordance with equation 1 set forth in the specification by analog calculation or other known equivalents for achieving adjustment of electronic signals relative to readings of a second electronic signal. Also, reference to "voltage" levels of the power source is exemplary; other electrical attributes might be referenced in the adjustment of duty cycles and/or the tracking of the "voltage" discharge cycle to achieve the same result; and accordingly such alternatives are intended to be encompassed with our reference to the term "voltage" in such contexts.

What is claimed is:

1. A method of controlling application of electrical power from a power source to heater elements of an electrically operated smoking system, said method comprising the steps of:

establishing in a controller of the electrical smoking system an executable power cycle comprising at least first and second differentiated phases, said establishing step providing each of said first and second differentiated phases with a preselected time period ($t_{phase}$), an adjustable duty cycle ($dc_{phase}$) and a preselected total energy ($J_{phase}$), respectively; and responsively to a puff on the smoking system, modulating power application to a heater element during each of said first and second differentiated phases in accordance with said established power cycle by:
   referencing a voltage of a power source; and
   adjusting said duty cycle of said phase responsively to said referencing step such that said respective preselected total energy level of said phase is achievable within said respective preselected time period of said phase.

2. The method as claimed in claim 1, wherein said referencing step comprises the step of referencing both voltage of said power source ($v_{in}$) and current through said heater element ($i_{heater}$) while applying power to said heater element during said phase.

3. The method as claimed in claim 2, wherein said duty cycle adjusting step comprises modulating a pulse density during said phase.

4. The method as claimed in claim 3, wherein said step of modulating pulse density comprises the steps of:

repetitively generating power pulses, each power pulse having a predetermined duration of on-time ($t_{on}$), said repetitively generating step including the step of interposing a duration of off-time ($t_{off}$) between consecutive power pulses; and adjusting said duration of off-time ($t_{off}$) during each of said phases responsively to said referencing step.

5. The method as claimed in claim 4, wherein said on-time ($t_{on}$) of said power pulses is less than approximately 0.010 second.

6. The method as claimed in claim 5, wherein said on-time ($t_{on}$) of said power pulses is approximately 0.008 second.

7. The method as claimed in claim 4, wherein said controller is provided with:

a first set of values indicative of said preselected time periods ($t_{phase}$) of said first and a second phases, respectively; and a second set of values relative to said preselected total energies ($J_{phase}$) of said first and a second phases, respectively, said second set of values indicative of a preselected target, average power level ($p_{phase}$) for said first and second phases, respectively;

said controller accessing respective values of $t_{phase}$ and $p_{phase}$ during each of said first and second phases, respectively; said controller executing said step of modulating pulse density during each said phase, respectively, by adjusting said duration of off-time ($t_{off}$), such that said controller applies power, for the respective time period ($t_{phase}$), to said heater element at a level approximating said respective target, average power level ($p_{phase}$).

8. The method as claimed in claim 7 further comprising the steps of:

when said duty cycle in any first phase reaches a 100% value, said controller executes said second phase at a 100% duty cycle until such time Tx that a total energy delivered during Tx approximately equals any difference between the preselected total energy of said first phase ($J_{phase\ 1}$) and actual energy delivery during said first phase together with an energy increment as originally determinable for the Tx portion of said second phase.

9. The method as claimed in claim 7, wherein said step of modulating pulse density includes resolving said duration of off-time ($t_{off}$) in accordance with the following relationship:

$$t_{off} = (i_{heater} \cdot v_{in} \cdot t_{on} / p_{phase}) - t_{on}.$$

10. The method as claimed in claim 8, wherein said on-time ($t_{on}$) of said power pulses is less than approximately 0.010 second.

11. The method as claimed in claim 7, wherein said step of modulating power application includes a plural execution of said referencing step during each respective phase, said step of adjusting $t_{off}$ in said respective phase being responsive to said plural referencing steps.

12. The method as claimed in claim 7 further comprising the step of establishing a predetermined range of voltages correlating to a voltage discharge cycle of said power source, said predetermined range including an upper operating voltage level and a lower operating voltage level, said method further comprising the step of limiting execution of said power cycle between said upper operating voltage level and said lower operating voltage level.

13. The method as claimed in claim 1, wherein said power cycle establishing step includes dividing a grand total cycle energy amongst said first and second phases, said total energy of said first phase being greater than said total energy of said second phase, said time period of said second phase being longer than said time period of said first phase.

14. The method as claimed in claim 7, wherein said power cycle establishing step includes dividing a grand total cycle energy amongst said first and second phases, said total energy of said first phase being greater than said total energy of said second phase, said time duration of said second phase being longer than said time duration of said first phase.

15. The method as claimed in claim 14, wherein said power cycle establishing step includes dividing said first phase into a plurality of sub-phases of progressively decreasing total energies.

16. The method as claimed in claim 1, wherein said step of repetitively executing said configured power cycle includes the step of modulating a power application by repetitively generating power pulses, each power pulse having a fixed period of time ($t_{on}$) throughout a substantial portion of said power cycle, said duty cycle adjusting step for each respective phase including the step of adjusting a total number of power pulses to be executed during the respective phase responsively to said voltage referencing step.

17. The method as claimed in claim 16, wherein said step of modulating power application includes delivering the respective energy ($J_i$) of each respective phase in accordance with the following analytical relationships:

$$f_i = (J_i/[t_{on} \cdot t_{phase\ i}]) \cdot (R_h/[v_{in} \cdot (R_h/(R_h+R_c)]^2); \text{ and}$$

$$dc_i = t_{on} \cdot f_i / t_{phase\ i};$$

wherein $f_i$ is the number of power pulses to be generated per second in the respective phase; $J_i$ is the preselected energy level of the respective phase; $t_{on}$ is the period of each power pulse; $R_h$ is an electrical resistance of the heater element; $R_c$ is an electrical resistance of circuitry of the controller; $t_{phase\ i}$ is the preselected time period of the respective phase; $v_{in}$ is a voltage level referenced from said plural voltage referencing step; and $dc_i$ is the duty cycle of the respective phase.

18. The method as claimed in claim 17 further comprising the step of electrically referencing at least one of the heater elements to obtain a reading indicative of a detected electrical resistance of said heater element and adjusting the value of $J_i$ in said analytical relationships in compensation of changes in said detected electrical resistance of said heater.

19. The method as claimed in claim 17, wherein said step of modulating power application includes a plural execution of said referencing step during each respective phase, said step of adjusting duty cycle in said respective phase being responsive to said plural referencing steps.

20. The method as claimed in claim 16 further comprising the step of establishing a predetermined range of voltages correlating to a voltage discharge cycle of said power source, said predetermined range including an upper operating voltage level and a lower operating voltage level, said method further comprising the step of limiting execution of said power cycle between said upper operating voltage level and said lower operating voltage level.

21. The method as claimed in claim 20, wherein said step of establishing a power cycle includes the step of preselecting a maximum value of duty cycle at a voltage level in a lower portion of said voltage discharge cycle.

22. The method as claimed in claim 21, wherein said step of preselecting said maximum value of duty cycle is established at a voltage level less than said lower operating voltage level.

23. The method as claimed in claim 16, wherein said power cycle establishing step includes dividing a grand total cycle energy amongst said first and second phases, said total energy of said first phase being greater than said total energy of said second phase, said time period of said second phase being longer than said time period of said first phase.

24. The method of claim 1, wherein said preselected time period ($t_{phase}$) of said first phase is different from said preselected time period ($t_{phase}$) of said second phase.

25. The method of claim 1, wherein said preselected total energy ($J_{phase}$) of said first phase is different from said preselected total energy ($J_{phase}$) of said second phase.

26. The method of claim 1, wherein said duty cycle adjusting step is effective for replicating a predetermined thermo-histogram.

27. The method of claim 1, wherein for a given voltage level of the power source voltage, a corresponding duty cycle associated with said first phase is different from a corresponding duty cycle associated with said second phase.

28. A method of controlling the application of power cycles in an electrical smoking system so that the smoking system provides consistent delivery, said smoking system including a source of electrical power, a plurality of heater elements and a controller for controllably communicating at least one of said heater elements with said electrical power source during a power cycle, said method comprising the steps of:

configuring a power cycle in accordance with a desired thermo-histogram, said configuring step including the steps of dividing said power cycle into at least first and second differentiated phases and establishing a respective time period for each phase and establishing a respective total energy for each phase;

establishing a predetermined range of voltages correlating to a discharge cycle of a power source, said predetermined range including an upper voltage level and a lower voltage level;

repetitively executing said configured power cycle upon demand by:
referencing a voltage of said power source; and
adjusting a respective duty cycle in each of said phases responsively to said referencing step such that the established, respective total energy of each phase is achieved during said execution step, whereby repetition of said desired thermo-histogram is achieved along said discharge cycle of said power source.

29. The method as claimed in claim 28, wherein said referencing step comprises the step of referencing both voltage of said power source ($v_{in}$) and current through said heater element ($i_{heater}$) while applying power to said heater element during said phase.

30. The method as claimed in claim 29, wherein said duty cycle adjusting step comprises modulating a pulse density during said phase.

31. The method as claimed in claim 30, wherein said step of modulating pulse density comprises the steps of:
repetitively generating power pulses, each power pulse having a predetermined duration of on-time ($t_{on}$), said repetitively generating step including the step of interposing a duration of off-time ($t_{off}$) between consecutive power pulses; and
adjusting said duration of off-time ($t_{off}$) during each of said phases responsively to said referencing step.

32. The method as claimed in claim 31, wherein said controller is provided with:
a first set of values indicative of said preselected time periods ($t_{phase}$) of said first and second phases, respectively; and
a second set of values relative to said preselected total energies ($J_{phase}$) of said first and a second phases, respectively, said second set of values indicative of a preselected target, average power levels ($p_{phase}$) for said first and second phases, respectively;
said controller accessing respective values of $t_{phase}$ and $p_{phase}$ during each of said first and second phases, respectively; said controller executing said step of modulating pulse density during each said phase, respectively, by adjusting said duration of off-time ($t_{off}$), such that said controller applies power, for the respective time period ($t_{phase}$), to said heater element at a level approximating said respective target, average power level ($p_{phase}$).

33. The method as claimed in claim 32 further comprising the steps of:
when said duty cycle in any first phase reaches a 100% value, said controller executes said second phase at a 100% duty cycle until such time Tx that a total energy delivered during Tx approximately equals any difference between the preselected total energy of said first phase ($J_{phase\ 1}$) and actual energy delivery during said first phase together with an energy increment originally determinable for the Tx portion of said second phase.

34. The method as claimed in claim 28, wherein said step of repetitively executing said configured power cycle includes the step of modulating a power application by repetitively generating power pulses, each power pulse having a fixed period of time ($t_{on}$) throughout a substantial portion of said power cycle, said duty cycle adjusting step for each respective phase including the step of adjusting a total number of power pulses to be executed during the respective phase responsively to said voltage referencing step.

35. The method as claimed in claim 34, wherein said step of modulating power application includes delivering the respective energy ($J_i$) of each respective phase in accordance with the following analytical relationships:

$$f_i = (J_i/[t_{on} \cdot t_{phase\ i}]) \cdot (R_h/[v_{in}*(R_h/(R_h+R_c)])^2); \text{ and}$$

$$dc_i = t_{on} \cdot f_i/t_{phase\ i};$$

wherein $f_i$ is the number of power pulses to be generated per second in the respective phase; $J_i$ is the preselected energy level of the respective phase; $t_{on}$ is the period of each power pulse; $R_h$ is an electrical resistance of the heater element; $R_c$ is an electrical resistance of circuitry of the controller; $t_{phase\ i}$ is the preselected time period of the respective phase; $v_{in}$ is a voltage level referenced from said plural voltage referencing step; and $dc_i$ is the duty cycle of the respective phase.

36. The method as claimed in claim 35 further comprising the step of electrically referencing at least one of the heater elements to obtain a reading indicative of a detected electrical resistance of said heater element and adjusting the value of $J_i$ in said analytical relationships in compensation of changes in said detected electrical resistance of said heater.

37. The method as claimed in claim 34 further comprising the step of limiting execution of said configured power cycle between said upper operating voltage level and said lower operating voltage level.

38. The method as claimed in claim 37, wherein said step of configuring a power cycle includes the step of preselecting a maximum value of duty cycle at a voltage level in a lower portion of said voltage discharge cycle.

39. The method as claimed in claim 38, wherein said step of preselecting said maximum value of duty cycle is established at a voltage level less than said lower operating voltage level.

40. The method as claimed in claim 28, wherein said power cycle configuring step includes dividing a total cycle energy among first and second phases, said respective energy level of said first phase being two-thirds of said total cycle energy, said respective energy level of said second phase being one-third of said total cycle energy.

41. The method of claim 28, wherein said time period of said first phase is different from said time period of said second phase.

42. The method of claim 28, wherein said total energy of said first phase is different from said total energy of said second phase.

43. The method of claim 28, wherein for a given voltage level of the power source voltage, a corresponding duty cycle associated with said first phase is different from a corresponding duty cycle associated with said second phase.

44. An electrical cigarette lighter comprising:
a source of electrical power having a predetermined range of voltages correlating to a discharge cycle of said power source, said predetermined range including an upper voltage level and a lower voltage level;
a plurality of heater elements adapted to receive a cigarette; and
a controller for controllably communicating at least one of said heater elements with said electrical power source responsively to a puff on said cigarette;
said controller configured to deliver electrical energy to said at least one heater in accordance with a predetermined power cycle including at least first and second differentiated phases, a preselected time period for each phase and a preselected energy level for each phase;
said controller including means for repetitively executing said configured power cycle, said means for repetitively executing said configured power cycle comprising:
means for referencing voltage of said power source; and
means for adjusting a respective duty cycle in each of said phases responsively to an output of said voltage referencing means such that the preselected energy level of each phase is achieved within said preselected time period of each phase during execution of said power cycle, whereby repetition of said predetermined power cycle is achieved along said discharge cycle of said power source.

45. The lighter as claimed in claim 44, wherein said means for repetitively executing said configured power cycle further comprises means for referencing current through said heater element ($i_{heater}$); said means for adjusting duty cycle comprising means for modulating a pulse density during each of said phases responsively to said voltage referencing means and said current referencing means.

46. The lighter as claimed in claim 45, wherein said means for modulating pulse density comprises:
   means for repetitively generating power pulses, each power pulse having a predetermined duration of on-time ($t_{on}$), together with a duration of off-time ($t_{off}$) being interposed between consecutive power pulses; and
   means for adjusting said duration of off-time ($t_{off}$) during each of said phases responsively to said voltage and current referencing means.

47. The lighter as claimed in claim 46, wherein said on-time ($t_{on}$) of said power pulses is less than approximately 0.010 second.

48. The lighter as claimed in claim 47, wherein said on-time ($t_{on}$) of said power pulses is approximately 0.008 second.

49. The lighter as claimed in claim 46, wherein said controller further comprises means for accessing:
   a first set of values indicative of said preselected time periods ($t_{phase}$) of said first and a second phases, respectively; and
   a second set of values of relative to said preselected total energies ($J_{phase}$) of said first and a second phases, respectively, said second set of values indicative of a preselected target, average power level ($p_{phase}$) for said first and second phases, respectively;
   said controller accessing respective values of $t_{phase}$ and $p_{phase}$ during each of said first and second phases, respectively; said modulating pulse density means adjusting said duration of off-time ($t_{off}$), such that said controller applies power, for the respective time period ($t_{phase}$), to said heater element at a level approximating said respective target, average power level ($p_{phase}$) during each said phase, respectively.

50. The lighter as claimed in claim 45, wherein said controller is configured to execute said second phase at a 100% duty cycle if said duty cycle in said first phase reached a 100% value, until such time Tx that a total energy delivered during Tx approximately equals any difference between the preselected total energy of said first phase ($J_{phase\ 1}$) and actual energy delivery during said first phase together with an energy increment as originally determinable for the Tx portion of said second phase.

51. The lighter as claimed in claim 45, wherein said controller is configured to limit execution of said power cycle between said upper operating voltage level and said lower operating voltage level.

52. The lighter as claimed in claim 45, wherein said power cycle establishing step includes dividing a grand total cycle energy amongst said first and second phases, said total energy of said first phase being greater than said total energy of said second phase, said time duration of said second phase being longer than said time duration of said first phase.

53. The lighter as claimed in claim 45, wherein said power cycle includes said first phase divided into a plurality of sub-phases of progressively decreasing total energies.

54. The electrical lighter as claimed in claim 44, wherein said controller includes means for repetitively generating power pulses, each power pulse having a fixed period of time ($t_{on}$) throughout a substantial portion of said power cycle, said duty cycle adjusting means including means for modulating a total number of power pulses to be executed during the respective phase responsively to the output of said voltage referencing means.

55. The electrical lighter as claimed in claim 54, wherein said fixed period of said power pulses is less than approximately 0.010 second.

56. The electrical lighter as claimed in claim 55, wherein said fixed period of said power pulses is less than approximately 0.008 second.

57. The electrical lighter as claimed in claim 54, wherein said voltage referencing means initially references the voltage of said power source as each respective phase is initiated, said modulating means being responsive to said initial referencing by said voltage referencing means.

58. The electrical lighter as claimed in claim 48, wherein said voltage referencing means references the voltage of said power source a plurality of times within each respective phase, said modulating means responsive to said plurality of referencing by said voltage referencing means.

59. The electrical lighter as claimed in claim 58, wherein said modulating means delivers the respective energy ($J_i$) of each respective phase in accordance with the following analytical relationships:

$$f_i = (J_i/[t_{on} \cdot t_{phase\ i}]) \cdot (R_h/[v_{in}*(R_h(R_h+R_c)]^2); \text{ and}$$

$$dc_i = t_{on} \cdot f_i/t_{phase\ i};$$

wherein $f_i$ is the number of power pulses to be generated per second in the respective phase; $J_i$ is the preselected energy level of the respective phase; $t_{on}$ is the period of each power pulse; $R_h$ is an electrical resistance of the heater element; $R_c$ is an electrical resistance of circuitry of the controller; $t_{phase\ i}$ is the preselected time period of the respective phase; $v_{in}$ is a voltage level referenced from said plural voltage referencing step; and $dc_i$ is the duty cycle of the respective phase.

60. The electrical lighter as claimed in claim 59 further comprising means for electrically referencing at least one of the heater elements to obtain a reading indicative of a detected electrical resistance of said heater element and adjusting the value of $J_i$ in said analytical relationships in compensation of changes in said detected electrical resistance of said heater.

61. The electrical lighter as claimed in claim 54, further comprising means limiting execution of said power cycle between said upper operating voltage level and said lower operating voltage level.

62. The electrical lighter as claimed in claim 61, wherein said modulating means establishes a maximum value of duty cycle at a voltage level in a lower portion of said voltage discharge cycle.

63. The electrical lighter as claimed in claim 62, wherein said step of preselecting said maximum value of duty cycle is established at a voltage level less than said lower operating voltage level.

64. The electrical lighter as claimed in claim 54, wherein said controller is configured to execute a total cycle energy with said first and second phases, said energy level of said first phase being two-thirds of said total cycle energy, said energy level of said second phase being one-third of said total cycle energy.

65. The electrical lighter as claimed in claim 44 further comprising a cigarette detector adapted to provide said controller a signal indicative of a cigarette being inserted into said lighter and puff sensor adapted to provide said controller a signal indicative of a smoker drawing upon the inserted cigarette;

said controller being configured to execute a preheating power cycle responsively to said controller receiving said signal that a cigarette has been inserted into the lighter, said preheating cycle comprising the steps of communicating electrical power to at least some of said heater elements in succession to deliver sufficient energy during said preheating power cycle to thermally pre-treat a portion of the inserted cigarette.

66. The electrical lighter as claimed in claim 65, wherein said energy of said preheating power cycle is in the range of approximately 5 to 25 Joules.

67. The electrical lighter as claimed in claim 64, wherein said energy of said preheating power cycle is in the range of approximately 10 to 25 Joules.

68. The electrical lighter as claimed in claim 66, wherein said energy of said preheating power cycle is approximately 17 Joules.

69. The method as claimed in claim 1, further comprising the step of establishing in said controller a preheating cycle executable upon said controller receiving a signal that a cigarette has been inserted into the lighter, said preheating cycle comprising the steps of communicating electrical power to at least some of said heater elements in succession to deliver sufficient energy during said preheating cycle to thermally pre-treat a portion of the inserted cigarette.

70. The method as claimed in claim 69, wherein said energy of said preheating cycle is in the range of approximately 5 to 25 Joules.

71. The method as claimed in claim 70, wherein said energy of said preheating cycle is in the range of approximately 10 to 25 Joules.

72. The method as claimed in claim 71, wherein said energy of said preheating cycle is approximately 17 Joules.

73. The electrical cigarette lighter of claim 44, wherein said preselected time period of said first phase is different from said preselected time period of said second phase.

74. The electrical cigarette lighter of claim 44, wherein said preselected energy level of said first phase is different from said preselected energy level of said second phase.

75. The electrical lighter of claim 44, wherein said means for adjusting the respective duty cycle in each of said phases is effective for replicating respective predetermined thermo-histograms in each of said phases.

76. The electrical lighter of claim 44, wherein for a given voltage level of the power source voltage, a corresponding duty cycle associated with said first phase is different from a corresponding duty cycle associated with said second phase.

77. An electrical lighter operative with a cigarette, said electrical lighter comprising:

a source of electrical power;

a plurality of heater elements adapted to receive a cigarette; and a cigarette detector adapted to provide said controller a first signal indicative of a cigarette being inserted into said lighter;

a puff sensor adapted to provide said controller a second signal indicative of a smoker drawing upon an inserted cigarette;

a controller configured to execute a puff-actuated power cycle of controllably communicating at least one of said heater elements with said electrical power source responsively to said second signal from said puff sensor;

said controller being further configured to execute a preheating power cycle upon said controller receiving said first signal from said cigarette detector, said preheating cycle comprising the steps of communicating electrical power to at least some of said heater elements in succession to deliver sufficient energy to thermally pre-treat a portion of the inserted cigarette.

78. The electrical lighter as claimed in claim 77, wherein said controller is configured to complete an execution of said preheating cycle prior to initiating said puff-actuated power cycle.

79. The electrical lighter as claimed in claim 77, wherein said energy of said preheating cycle is in the range of approximately 5 to 25 Joules.

80. The electrical lighter as claimed in claim 29, wherein said energy of said preheating cycle is in the range of approximately 10 to 25 Joules.

81. The electrical lighter as claimed in claim 80, wherein said energy of said preheating cycle is approximately 17 Joules and the time duration of each power communication is approximately ⅛ second.

82. The electrical lighter as claimed in claim 81, wherein said the time duration of each power communication is approximately ⅛ second for each of eight heaters.

\* \* \* \* \*